United States Patent [19]

Hart et al.

[11] Patent Number: 5,620,687
[45] Date of Patent: Apr. 15, 1997

[54] INHIBITION OF INTIMAL HYPERPLASIA USING ANTIBODIES TO PDGF BETA RECEPTORS

[75] Inventors: Charles E. Hart, Brier; Richard D. Kenagy; Alexander W. Clowes, both of Seattle, all of Wash.

[73] Assignees: ZymoGenetics, Inc.; University of Washington, both of Seattle, Wash.

[21] Appl. No.: 366,860

[22] Filed: Dec. 30, 1994

Related U.S. Application Data

[63] Continuation-in-part of Ser. No. 304,623, Sep. 12, 1994, abandoned, which is a continuation of Ser. No. 23,504, Feb. 25, 1993, abandoned.

[51] Int. Cl.$^6$ .................................................. A61K 39/395
[52] U.S. Cl. .................................... 424/143.1; 424/130.1; 424/133.1; 424/135.1; 424/152.1
[58] Field of Search .......................... 424/130.1, 133.1, 424/135.1, 136.1, 141.1, 143.1, 145.1, 158.1, 152.1

[56] References Cited

U.S. PATENT DOCUMENTS

| | | | |
|---|---|---|---|
| 5,155,027 | 10/1992 | Sledziewski | 435/69.7 |
| 5,171,217 | 12/1992 | March et al. | 604/53 |
| 5,250,519 | 10/1993 | Conrad et al. | 514/56 |
| 5,268,358 | 12/1993 | Fretto | 514/12 |

FOREIGN PATENT DOCUMENTS

| | | |
|---|---|---|
| 568310 | 11/1993 | European Pat. Off. |
| 93/10805 | 6/1993 | WIPO |
| 94/16706 | 8/1994 | WIPO |
| 94/21689 | 9/1994 | WIPO |

OTHER PUBLICATIONS

Clowes et al., *Circulation Research* 58(6): 839–845, 1986.
Currier et al., *JACC* 17(6): 118B–125B, 1991.
Schmid et al., *Seminars in Thrombosis and Hemostasis* 19 Suppl. 1,: 155–159, 1993.
Edelman et al., *Proc. Natl. Acad. Sci. U.S.A.* 87: 3773–3777, 1990.
Rubin et al., *The Lancet* 1(8599): 1353–1356, 1988.
Ferns et al., *Science* 25: 1129–1132, 1991.
Linder et al., *J. Clin. Invest.* 85:2004–2008, 1990.
Jawien et al., *J. Clin. Invest.* 89: 507–511, 1992.
Linder et al., *J. Clin. Invest.* 90: 2044–2049, 1992.
Popma et al., *Circulation* 84(3): 1426–1436, 1991.
Ferrell et al., *Circulation* 85(4): 1630–1631, 1992.
Reilly et al., *J. Cell. Phys.* 136: 23–32, 1988.
Guyton et al., *Circulation Research* 46(5): 625–634, 1980.
Cavari et al., *Cell Biology International* 17(8): 781–786, 1993.
Kimura et al., *Japan. J. Pharmacol.* 59: 51–56, 1992.
Castellot, Jr. et al., *J. Cell. Biol.* 109(6): 3147–3155, 1989.
*Bioworld Today* 5(4): 1, 3; 1994.
Buchwald et al., *Circulation* 86(2): 531–537, 1992.
Harris et al. *TIBTECH* 11: 42–44(1993).
Mullins *Arterioscler Thromb* 14:1047–1055 (1994).
DeFeudis *DN&P* 5(1) 49–51 (1992).
Kelly et al. *J Biol Chem.* 266 8987–8992(1991).
Kawahara et al. *Biochem Biophys Res Commun* 147:839–845 (1987).

Primary Examiner—Christina Y. Chan
Assistant Examiner—Phillip Gambel
Attorney, Agent, or Firm—Gary E. Parker; Debra K. Leith; Deborah A. Sawislak

[57] ABSTRACT

Methods for inhibiting intimal hyperplasia in the vasculature of mammals, including primates, are disclosed. The methods comprise administering to the mammal an anti-PDGF receptor antibody, such as an anti-PDGF-alpha receptor antibody or an anti-PDGF-beta receptor antibody. The methods are useful in reducing intimal hyperplasia due to, for example, vascular injuries resulting from angioplasty, endarterectomy, reduction atherectomy or anastomosis of a vascular graft. The anti-PDGF receptor antibodies may optionally be administered coordinately with heparin, whereby the coordinately administered antibody and heparin are combinatorially effective in inhibiting intimal hyperplasia.

19 Claims, 12 Drawing Sheets

INHIBITION OF INTIMAL HYPERPLASIA USING ANTIBODIES TO PDGF BETA RECEPTORS

GOVERNMENT SUPPORT

This invention was made with government support under grant number NIH HL 30946 awarded by the National Institutes of Health. The government has certain rights in the invention.

CROSS-REFERENCE TO RELATED APPLICATIONS

This application is a continuation-in-part of U.S. patent application Ser. No. 08/304,623, filed Sep. 12, 1994 and incorporated herein by reference in its entirety, which application is abandoned and which is a continuation of Ser. No. 08/023,504, filed Feb. 25, 1993 and now abandoned.

TECHNICAL FIELD

The present invention relates to methods for inhibiting intimal hyperplasia, including restenosis, in a mammal following vascular injury, and to compositions useful within those methods.

BACKGROUND OF THE INVENTION

Proliferation of smooth muscle cells (SMCs) in the vessel wall is an important event in the formation of vascular lesions in atherosclerosis, after vascular reconstruction or in response to other vascular injury. For example, treatment of atherosclerosis frequently includes the clearing of blocked vessels by angioplasty, endarterectomy or reduction atherectomy, or by bypass grafting, surgical procedures in which atherosclerotic plaques are compressed or removed through catheterization (angioplasty), stripped away from the arterial wall through an incision (endarterectomy) or bypassed with natural or synthetic grafts. These procedures remove the vascular endothelium, disturb the underlying intimal layer, and result in the death of medial SMCs. This injury is followed by medial SMC proliferation and migration into the intima, accompanied by excessive deposition of extracellular matrix. This lesion development characteristically occurs within the first few weeks and up to six months after injury and stops when the overlying endothelial layer is reestablished. In humans, these lesions are composed of about 20% cells and 80% extracellular matrix.

In about 30% or more of patients treated by angioplasty, endarterectomy or bypass grafts, thrombosis and/or SMC proliferation in the intima causes re-occlusion of the vessel and consequent failure of the reconstructive surgery. This closure of the vessel subsequent to surgery is known as restenosis.

A similar process of SMC proliferation has also been observed in organ transplants, and may contribute to transplant atherosclerosis and organ failure. The intimal thickening in this process involves only the grafted organ.

It has been postulated that platelet mitogens, such as platelet derived growth factor (PDGF), play a role in the development of atherosclerotic plaques (see Ross et al., *Cell* 46: 155–169, 1986; Harker, *Am. J. Cardiol.* 60: 20B–28B, 1987). One proposed mechanism for plaque formation is the release by platelets, at sites of endothelial denudation, of growth factors that stimulate SMC growth (Ross and Glomset, *N. Eng. J. Med.* 295: 369–377, 420–425, 1976; Ross, *Arteriosclerosis* 1: 293–311, 1981). Moore et al. (*Thrombos. Haemostas.* (Stuttg.) 35: 70, 1976) and Friedman et al. (*J. Clin. Invest.* 60: 1191–1201, 1977), using an indwelling catheter injury model, reported an inhibition of experimentally induced intimal lesion formation in rabbit arteries by prolonged thrombocytopenia induced by administration of anti-platelet serum. It has also been postulated that SMCs may themselves produce PDGF which stimulates lesion development through an autocrine mechanism (Ross et al., ibid; Walker et al., *Proc. Natl. Acad. Sci. USA* 83: 7311–7315, 1986). Fingerle et al. (*Proc. Natl. Acad. Sci. USA* 86: 8412–8416, 1989) investigated intimal lesion formation in thrombocytopenic rats and concluded that platelets do not play a role in the initial SMC proliferation after balloon injury but may regulate SMC migration into the intima. Platelets are now known to release a number of growth factors, including PDGF, epidermal growth factor (EGF), transforming growth factors alpha and beta (TGFα and TGFβ), insulin-like growth factor I (IGF-I) and platelet derived endothelial cell growth factor, as well as several chemoattractant molecules. Although certain studies implicate PDGF in processes associated with lesion development, no studies have shown the participation of PDGF in these processes in primates.

Removal of atherosclerotic plaques by angioplasty or endarterectomy has limited efficacy, and no effective treatment for restenosis of treated vessels or stenosis of bypass grafts has been developed. There is therefore a need in the art for methods of reducing or preventing the development of SMC-rich lesions in vascular walls, including stenosis of blood vessels following vascular injury, such as injury due to balloon catheterization, endarterectomy or reduction atherectomy, as well as in vascular grafts, organ transplants and catheter emplacements. The present invention provides such methods and fulfills other, related needs.

DISCLOSURE OF THE INVENTION

The present invention provides methods and compositions for inhibiting intimal hyperplasia in the vasculature of a mammal, particularly a primate. Examples of intimal hyperplasia include restenosis following angioplasty, endarterectomy or other procedures whereby atherosclerotic plaques are removed from blood vessels. The methods of the invention generally comprise administering to a mammal an effective amount of an anti-growth factor receptor antibody to inhibit intimal hyperplasia. Suitable anti-growth factor receptor antibodies include antibodies to fibroblast growth factor (FGF) receptors, transforming growth factor beta (TGF-β) receptors, insulin-like growth factor I (IGF-I) receptors, epidermal growth factor (EGF) receptors, thrombin receptors and factor Xa receptors.

It is preferred within the present invention to utilize an anti-platelet derived growth factor (PDGF) receptor antibody in an amount sufficient to inhibit mitogenesis and/or migration of smooth muscle cells. An anti-PDGF receptor antibody may be administered alone, in combination with other anti-PDGF receptor antibodies, in combination with antibodies to other receptors, or in combination with a heparin.

Within one aspect of the invention, intimal hyperplasia is inhibited by administering to a mammal an effective amount of an anti-PDGF receptor antibody, such as an anti-PDGF-alpha receptor antibody, an anti-PDGF-beta receptor antibody, or a panel of anti-PDGF receptor antibodies. Within one embodiment, the panel of antibodies is capable of inhibiting the binding of the AA, AB and BB isoforms of PDGF to PDGF receptors.

Within another aspect of the invention, an anti-PDGF receptor antibody is administered to a mammal concurrently with, or within an antihyperplastically effective time period prior to, an occurrance of an acute vascular injury in the mammal. Examples of acute vascular injuries include vascular reconstruction procedures such as angioplasty, endarterectomy, reduction atherectomy and anastomosis of a vascular graft. In a related aspect, the antibody is administered concurrently with, or within an antihyperplastically effective time period prior to, emplacement of a vascular graft or transplanted organ. Within other embodiments, the antibody is administered within an antihyperplastically effective time period following an occurance of an acute vacular injury or emplacement of a vascular graft or transplanted organ.

Within another aspect of the invention, the antibodies are used to inhibit intimal hyperplasia that occurs within a vascular graft or transplanted organ.

Within another aspect of the invention, intimal hyperplasia in the vasculature of a mammal is inhibited by coordinately administering to the mammal an anti-growth factor receptor antibody, such as an anti-PDGF receptor antibody, and heparin in respective amounts of antibody and heparin sufficient to combinatorially inhibit the hyperplasia. The antibody and heparin are administered concurrently or, alternatively, sequentially with either the antibody or heparin administered first, and the nonadministered remainder of the antibody and heparin administered within an effective time period thereafter.

Within related embodiments, the coordinately administered antibody and heparin combinatorially inhibit one or more of the intimal hyperplastic processes of vascular smooth muscle cell proliferation, vascular smooth muscle cell migration, and/or neointimal deposition of extracellular matrix. Within further embodiments, the antibody is either an anti-PDGF-alpha receptor antibody, an anti-PDGF-beta receptor antibody, or a panel of anti-PDGF receptor antibodies. Within additional embodiments, the antibody inhibits a receptor function of the growth factor receptor, such as binding of the receptor to a receptor ligand, or dimerization of the growth factor receptor. Within other embodiments, an anti-PDGF antibody is administered which inhibits binding of one or more of the AA, AB and BB isoforms of PDGF to PDGF receptors. Within other embodiments, the heparin comprises a heparan sulfate or a low molecular weight heparin characterized by having a reduced anti-thrombotic activity.

Within other aspects of the invention, an anti-PDGF receptor antibody and heparin are coordinately administered to a mammal concurrently with, or within an effective time period before, an occurrence of an acute vascular injury in the mammal. Acute vascular injuries include vascular injuries arising from vascular reconstruction, including injuries due to angioplasty, endovascular stenting, endarterectomy, endovascular laser ablation, reduction atherectomy or anastomosis of a vascular graft. In related aspects, the antibody and heparin are administered concurrently with, or within a therapeutically effective time period before, emplacement of a vascular graft or transplanted organ. Within other embodiments, the antibody and heparin are administered within an antihyperplastically effective time period following an occurance of an acute vacular injury or emplacement of a vascular graft or transplanted organ.

Within yet another aspect of the invention, pharmaceutical kits are provided for the treatment of intimal hyperplasia in a mammal, which kits include an anti-PDGF receptor antibody and heparin in a pharmacologically suitable carrier. In one embodiment, the antibody and heparin are precombined in a single carrier. In another embodiment, the antibody and heparin are administrable by simultaneous, separate or sequential delivery.

Antibodies useful within the present invention include monoclonal antibodies and genetically engineered antibodies, the latter including single chain antibodies, chimeric antibodies, bifunctional antibodies and immunoconjugates.

Heparin preparations useful within the present invention include unfractionated or fractionated heparins and heparin-like glycosaminoglycans, including heparan sulfates. Also useful are low molecular weight heparins, including anticoagulant and nonanticoagulant fragments and derivatives of heparin and heparin-like glycosaminoglycans.

These and other aspects of the invention will become evident upon reference to the following detailed description and the attached drawings.

DETAILED DESCRIPTION OF THE INVENTION

Figure 1:
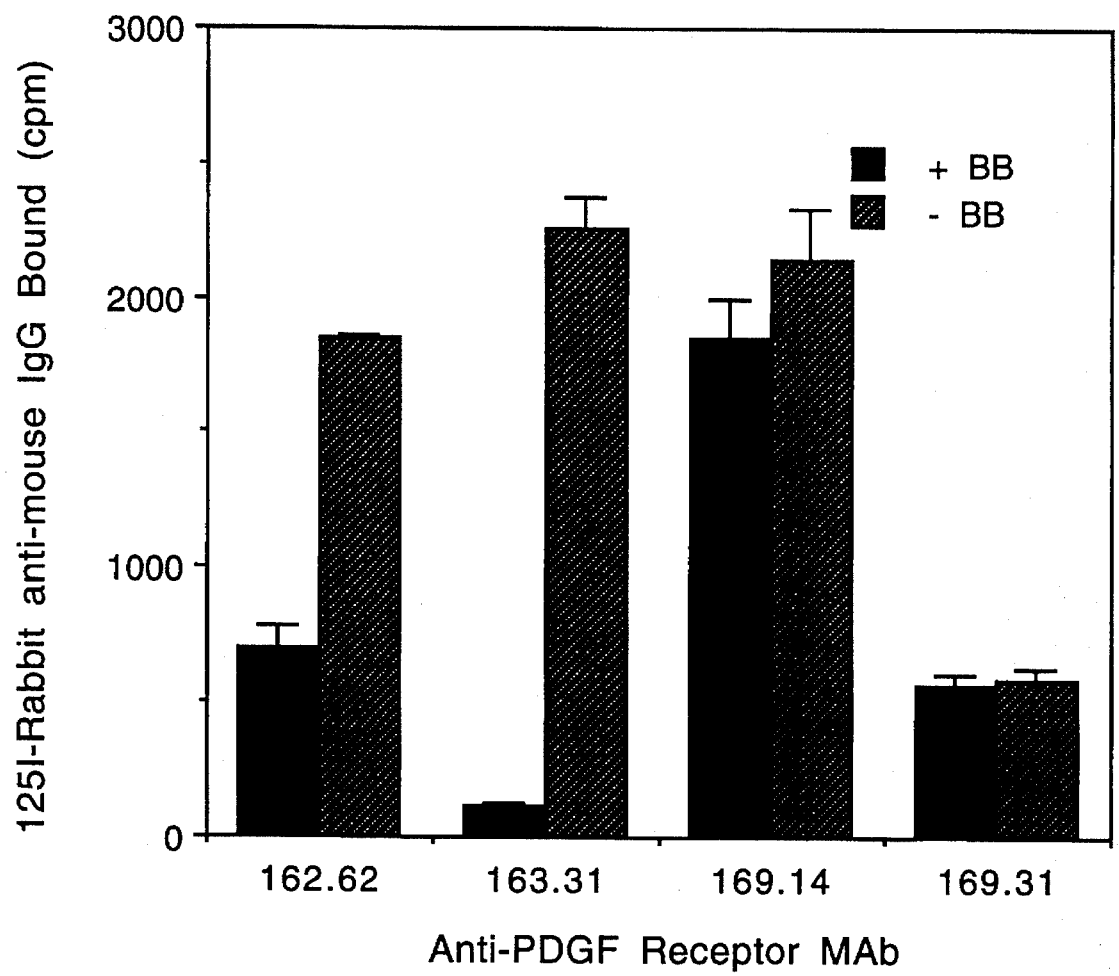
FIG. 1 illustrates the binding of anti-PDGF receptor monoclonal antibodies to cells that express recombinant PDGF-beta receptor. Results are expressed as mean cpm bound of $^{125}$I-rabbit anti-mouse IgG for triplicate determinations. The bars indicate standard deviation.

As noted above, restenosis of blood vessels is a common problem in patients who have undergone angioplasty, endarterectomy, or bypass grafting. Restenosis is one example of intimal hyperplasia, which is believed to proceed via a process that includes both proliferation (mitosis) and migration of vascular smooth muscle cells in the area damaged by the surgical procedure, as well as by the production (deposition) of extracellular matrix. See, in general, (Harker, *Am. J. Cardiol.* 60:20B–28B, 1987; DeFeudis, *Drug News and Perspectives* 5:49–51, 1992). This proliferative process is also manifested in the occlusion of vascular grafts (both natural, including autologous and allogeneic, and synthetic), and in transplanted organs. This proliferative process results in the development of lesions rich in smooth muscle cells and is refered to herein as intimal hyperplasia.

The present invention provides methods for inhibiting the development of SMC-rich lesions through the use of antibodies against growth factor receptors, preferably PDGF receptors. Such lesions result in the partial or complete blocking of a blood vessel through intimal thickening (hyperplasia). Inhibition of intimal hyperplasia will be understood to include interfering with the proliferative process by reducing or preventing one or more hyperplastic processes, including cell migration, cell proliferation, and extracellular matrix formation. By blocking proliferation and/or migration through interfering with the interaction of PDGF and its receptors, SMC proliferation and subsequent matrix deposition may be reduced. A reduction in intimal hyperplasia is clinically manifested as a significant decrease in loss of lumenal volume after an acute vascular injury. Such a reduction will generally result in a decreased need for re-vascularization procedures (e.g., repeat angioplasty) at the site of the initial injury.

The methods of the present invention are particularly useful in the treatment of intimal hyperplasia due to acute vascular injury. Acute vascular injuries are those which occur rapidly (i.e. over days to months), in contrast to chronic vascular injuries (e.g. atherosclerosis) which develop over a lifetime. Acute vascular injuries often result from surgical procedures such as vascular reconstruction, wherein the techniques of angioplasty, endarterectomy, atherectomy, vascular graft emplacement or the like are employed. Hyperplasia may also occur as a delayed response in response to, e.g., graft emplacement or organ transplantation.

Antibodies useful within the present invention may be produced by conventional procedures of immunization and purification. Briefly, a PDGF receptor, receptor fragment or fusion protein comprising a receptor polypeptide, preferably purified, is administered to an animal such as a mouse, rat, rabbit or goat in an amount sufficient to cause an immune response. It is preferred to administer the growth factor receptor in combination with an adjuvant, such as Freund's adjuvant, in order to enhance the immune response. Although a single injection of antigen may be sufficient to induce antibody production in the animal, it is generally preferred to administer a large initial injection followed by one or more booster injections over a period of several weeks to several months. See, e.g., Hurrell, J. G. R., ed., *Monoclonal Hybridoma Antibodies: Techniques and Applications,* CRC Press Inc., Boca Raton, Fla., 1982, which is incorporated herein by reference. Blood is then collected from the animal and clotted, and antibodies are isolated from the serum using conventional techniques such as salt precipitation, ion exchange chromatography, affinity chromatography or high performance liquid chromatography.

Within one embodiment of the invention, monoclonal antibodies are used. Monoclonal antibodies provide the advantages of ease of production and lower therapeutic doses as compared to polyclonal antisera, since only antibodies of the desired specificity are used. Methods for producing monoclonal antibodies are well known in the art and are disclosed, for example, by Kohler and Milstein (*Nature* 256: 495, 1975; *Eur. J. Immunol.* 6: 511–519, 1976). See also Hurrell, J. G. R., ed., *Monoclonal Hybridoma Antibodies: Techniques and Applications,* CRC Press Inc., Boca Raton, Fla., 1982 and Hart, U.S. Pat. No. 5,094,941. As will be appreciated by those skilled in the art, antibody fragments, such as Fab fragments, may also be used.

It is generally preferred to use antibodies that are syngenesious with the patient or that contain syngenesious constant regions. For this reason, genetically engineered antibodies that contain human framework structures will generally be used in the treatment of humans. Methods for producing recombinant human antibodies or humanized non-human (i.e. chimeric) antibodies are disclosed by Cabilly et al. (U.S. Pat. No. 4,816,567), Robinson et al. (WO 87/02671) and Neumaier (WO 90/00616), which are incorporated herein by reference. Briefly, human constant region genes are joined to appropriate human or non-human variable region genes. For example, the amino acid sequences which represent the antigen binding sites (CDRs, or complimentarity-determining regions) of the parent murine monoclonal antibody are grafted at the DNA level onto human variable region framework sequences. This process is known as "humanization". Methods for this technique are known in the art and are disclosed, for example, by Jones et al. (*Nature* 326: 522–525, 1986), Riechmann et al. (*Nature* 322: 323–327, 1988) and Queen et al. (*Proc. Natl. Acad. Sci. USA* 86: 10029–10033, 1989).

The joined genes are then transfected into host cells, which are cultured according to conventional procedures. In the alternative, monoclonal antibody producing cells are transfected with cloned human constant region genes, and chimeric antibody genes are generated by homologous recombination. Thus it is possible to assemble monoclonal antibodies with a significant portion of the structure being human, thereby providing antibodies that are more suitable for multiple administrations to human patients.

Alternatively, a single chain antibody may be developed through the expression of a recombinant polypeptide which is generally composed of a variable light-chain sequence joined, typically via a linker polypeptide, to a variable heavy-chain sequence. Methods for producing single chain antibodies are known in the art and are disclosed, for example, by Davis et al. (*BioTechnology* 9: 165–169, 1991).

Two PDGF receptor polypeptides have been described. These are termed "alpha receptor" (Kelly et al., WO 90/14425; Kelly et al., U.S. Pat. No. 5,371,205; Claesson- Welsh et al., *Proc. Natl. Acad. Sci. USA* 86: 4917–4921, 1989) and "beta receptor" (Claesson-Welsh et al., *Mol. Cell. Biol.* 8: 3476–3486, 1988; Gronwald et al., *Proc. Natl. Acad. Sci. USA* 85: 3435–3439, 1988). In the presence of PDGF ligand, the receptor polypeptides dimerize. Three receptor subtypes are thus possible: $\alpha\alpha$, $\alpha\beta$ and $\beta\beta$. The $\beta$ receptor is specific for the B-chain of PDGF, while the $\alpha$ receptor binds the A-chain and the B-chain. Consequently, the growth regulatory responsiveness of cells to PDGF depends not only on the availability of PDGF AA, AB and BB ligand isoforms, but also on the expression and availability of different PDGF receptor subtypes (Heldin et al., *Cell Regul.* 1: 555–566, 1990). Human smooth muscle cells express both $\alpha$ and $\beta$ receptor subtypes (Heldin et al., *Cell Regul.* 1: 555–566, 1990), but other cell types are known which express only a single receptor subtype (Gronwald et al., *J. Biol. Chem.* 264: 8120–8125, 1989).

The anti-PDGF receptor antibodies used within the present invention will preferably be a panel of antibodies capable of inhibiting all three PDGF receptor isoforms ($\alpha\alpha$, $\beta\beta$ and $\alpha\beta$). As used herein, the term "panel" denotes a combination of two or more antibodies having different specificities. The antibodies may be specific for different antigens or for different epitopes on a single antigen. Monoclonal antibodies (MAbs) are preferred.

As noted above, antibodies used within the present invention interfere with the interaction of PDGF and its receptors. In preferred embodiments of the invention, anti-PDGF receptor antibodies are employed which inhibit binding of a PDGF ligand to a PDGF receptor, although those skilled in the art will recognize that the advantages of the invention can also be realized using antibodies that inhibit other receptor-ligand interactions, such as receptor dimerization.

Anti-receptor monoclonal antibodies may also be used as targeting agents for the delivery of compounds of therapeutic interest. Such compounds include, but are not limited to, toxins, cytostatic compounds, or proenzymes whose potential function can be to activate endogenous proenzymes, to activate proenzymes added from exogenous sources, or to activate enzyme cleavage sites on prodrugs. Anti-receptor antibodies can also be labeled with radionucleotides, dyes, fluorescent compounds or the like for use as imaging agents. Examples of this include imaging sites of thrombosis, or sites of vascular injury where there is exposure, by example, of vascular smooth muscle cells which express cell-surface receptors.

Monoclonal antibodies can also be used to develop bifunctional antibodies where there are two independent antigenic binding sites on each immunoglobulin molecule. This technology is known in the art and has been disclosed in the literature (*Thromb. Res. Suppl. X:* 83, 1990). Additionally, bispecific antibodies can also be constructed from single chain antibodies. This technology is known in the art and has been disclosed, for example, by A. George (*The Second Annual IBC International Conference on Antibody Engineering,* Dec. 16–18, 1991, San Diego, Calif.).

Antibodies used within the present invention will be able to block a significant amount of the biological activity of an antigen in an in vitro test system, e.g. the ability to block the interaction of one or more PDGF ligands with PDGF receptor(s). Suitable in vitro test systems include, inter alia, mitogenesis assays and receptor binding assays. For example, 25 µg/ml of a monoclonal anti-PDGF-alpha receptor MAb described herein is able to block the mitogenic activity of 10 ng/ml of PDGF-AA. As will be understood by those skilled in the art, the amount of antibody needed to inhibit the activity of a given amount of antigen will depend on such factors as antibody specificity and affinity. It is preferred not to block 100% of serum mitogenic activity so that not all of the wound healing response is suppressed. Antibody doses are calculated as described below, taking into consideration affinity and specific activity.

An "antihyperplastically effective amount" of an anti-PDGF receptor antibody is defined as an amount sufficient to measurably reduce or prevent intimal hyperplasia in a blood vessel, vessel graft or vascular component of a transplanted organ. More specifically, "inhibition of intimal hyperplasia" is herein defined to include any measurable inhibition of one or more of the intimal hyperplastic processes described in the art as vascular smooth muscle cell (VSMC) migration, VSMC proliferation, and neointimal deposition of extracellular matrix. In this context, reduction or prevention of intimal hyperplasia, or of a hyperplastic process involved in intimal hyperplasia, can be readily evaluated using in vitro, in vivo and ex vivo assay systems known in the art, in particular primate-based assay systems (e.g., non-human or human primate VSMC cultures or vascular tissue explants, or non-human primate in vivo tests). In interpreting in vitro dosage data, it will be appreciated that different test cells and tissues may express different levels and/or types of PDGF receptors. In addition, cell culture passage number (i.e. number of cell generations elapsed following dissociation or outgrowth of VSMCs from a vascular tissue source) will be recognized as potentially having an important impact on mitogenic and other growth-related activities observed in experimental systems. Similarly, a number of variables must be considered in extrapolating in vivo data from non-human systems to estimate antihyperplastic effectiveness of antibodies in humans. In particular, it is important to consider any differences in the nature and severity of a blood vessel injury between experimental and clinical systems to best utilize model data in determining actual treatment protocols for humans. Likewise, interspecies differences in vascular anatomy and histology, and intrinsic differences in the hyperplastic processes triggered by different kinds of vascular injuries, must be weighed when extrapolating between model and clinical applications. Nevertheless, the assays and methods described herein, including the in vitro and in vivo studies using non-human and human primate model systems, provide all of the necessary guidance, coupled with known techniques including standard clinical trial procedure, to determine successful treatment protocols for intimal hyperplasia in mammalian patients, including humans.

It is preferred that the antihyperplastically effective amount of antibody significantly inhibit proliferation (e.g., as determined in an in vitro mitogenesis assay) and/or migration of vascular smooth muscle cells. A "significant" reduction is a reduction of mitogenesis or migration of 50% or more in an in vitro assay. While the actual amount will depend in part on such factors as the specificity and binding affinity of a particular antibody, an effective amount can be determined empirically by in vitro and ex vivo procedures known in the art and disclosed herein. In general, amounts of antibody for therapeutic use will be sufficient to provide a concentration in the bloodstream or at the site of action at least equal to that shown to be effective in vitro or ex vivo. It is preferred, however, to use higher amounts in vivo, up to or exceeding an order of magnitude increase. Thus, in model systems, anti-PDGF receptor antibody dosage is selected with the goal of providing temporary or persistent, local or systemic levels of antibody in the treated mammal which correspond to antibody concentrations shown to be antihyperplastically effective in suitable in vitro tests.

Of particular interest for in vivo testing is a baboon vascular injury model disclosed in detail herein. This model has been designed to mimic the injury response that occurs in humans following various types of acute treatments to open occluded arteries. The use of balloon angioplasty for the generation of a vascular lesion mimics a procedure that is commmonly used to re-establish blood flow in stenosed coronary arteries and which leads to restenosis in 30–40% of treated individuals. This model is therefore particularly well suited for testing the use of anti-PDGF receptor antibodies, alone or in conjunction with heparin.

Another suitable model for testing the efficacy of anti-PDGF receptor antibody therapy is a baboon model of carotid endarterectomy. In this model an acute injury is made to the medial area of the artery, which subsequently leads to the development of an intimal lesion (Hanson et al., *Hypertension* 18:1170–1176, 1991). This model mimics the use of carotid endarterectomy to open carotid arteries in humans that have decreased blood flow due to advanced atherosclerosis. A third model for testing the use of anti-PDGF receptor antibody therapy is a baboon vascular graft emplacement model. It has been demonstrated that the placement of vascular grafts leads to the generation of hyperplastic lesions at the site of the graft (Kraiss et al., *J. Clin. Invest.* 92:338–348, 1993). These lesions have characteristics similar to those of hyperplastic lesions in humans at sites of vascular injuries.

To test the efficacy of anti-PDGF receptor antibody therapy in humans, various types of analysis can be used. These include monitoring for a loss in mean lumenal diameter (MLD) by angiography at the 3–6 month period following vascular treatment. Alternative methods to monitor efficacy include intravascular ultrasound, B-mode ultrasound and magnetic resonance imaging. Clinical correlates can also be used to monitor for efficacy of the anti-PDGF receptor antibody treatment. These include a decrease in myocardial infarcts and recurent angina, and the need for repeat re-vascularization.

Antibody dosage levels are calculated from inhibition data after determining clearance of antibody from the blood. In general, dosage is selected with the goal of maintaining circulating levels of antibody sufficient to inhibit greater than 10%, preferably at least 20–50% of circulating PDGF activity (e.g., receptor-ligand binding, PDGF- or serum-stimulated mitogenesis and/or migration of VSMCs, or another biological activity correlated with PDGF receptor function and/or regulation of an intimal hyperplastic process). In general, doses will be in the range of about 0.1 µg to 500 mg or more of antibody per kg of patient body weight per day, preferably about 20 µg to 20 mg/kg/day, more preferably about 1 mg–10 mg/kg/day. As noted above, the actual dose will depend in part on antibody affinity and activity. Somewhat higher doses may be required if two or more antibodies are administered in combination than if a single antibody is used. To minimize antibody production costs and limit immuno-intolerance of administered antibodies by the patient, it is preferred to use high affinity antibodies having a high specific inhibitory activity, enabling the use of doses of about 1 mg/kg/day or less.

In humans treated with anti-PDGF receptor antibody therapy, either alone, or in combination with heparin, the antibody may be given under a wide range of conditions. The antibody can be given via bolus injections, both prior to the re-vascularization procedure as well as multiple times following the procedure. The antibody may be given as a bolus injection (intravenous, intramuscular, intraperitoneal or subcutaneous) prior to the procedure (generally within 24 hours before surgery) and a constant infusion following the procedure (including infusion via implanted pumps). In many cases it will be preferable to administer daily doses (including administration by infusion) during a hospital stay, followed by less frequent bolus injections during a period of outpatient treatment of one to two weeks or more. Treatment may be continued for up to six months after initial injury. The antibody may be given via multiple routes including intravenous, intramuscular or subcutaneous injections. In addition the antibody may be delivered locally to the site of vascular injury using perfusion balloon catheters, coating onto stents, or placement on gel coated balloons. In the latter cases it would be expected that the doses of antibody would be substantially less than that required when given systemically. The antibodies may also be delivered by slow-release delivery systems, including such systems incorporated into vascular grafts or stents, or by way of perfusion or double balloon catheters. For inhibition of stenosis in vascular grafts, anti-PDGF receptor antibodies may be covalently attached to the graft through their constant regions or incorporated into the graft in slow-release formulations. Pumps and other known delivery systems may also be employed. In any event, administration is designed to provide the desired daily dose (e.g., a five-day bolus of 25 mg/kg to provide 5 mg/kg/day).

For use within the present invention, anti-PDGF receptor antibodies are formulated into injectable compositions according to conventional procedures and packaged in sterile containers. The antibodies may be combined with a suitable diluent such as sterile saline or sterile water. The antibody compositions may further contain carriers, stabilizers and excipients such as sugars (e.g. mannitol) or albumin. In the alternative, the antibodies may be provided in lyophilized form and reconstituted in a suitable diluent prior to use. These compositions may be packaged in single or multiple dosage form, for example in sealed ampoules or vials.

In an alternate embodiment of the invention, an anti-growth factor receptor antibody, such as an anti-PDGF receptor antibody, is administered to a mammal coordinately with heparin, in respective unit doses of antibody and heparin sufficient to combinatorially inhibit intimal hyperplasia in the vasculature of the mammal. In this context, "coordinate administration" is intended to include concurrent, separate or sequential adminstration of the antibody and heparin, wherein both the antibody and heparin are administered within a limited, combinatorially effective time period relative to one another. A "combinatorially effective time period" is defined as a maximum intervening time period between administration of the antibody and administration of the heparin in which the two agents are combinatorially effective in inhibiting the hyperplasia. The term "combinatorially effective" is in turn defined as producing a measurable inhibition of intimal thickening or lesion formation, or of a hyperplastic process, which exceeds a maximum level of inhibition independently provided by either the antibody or heparin administered alone, under otherwise comparable conditions and dose.

As used herein, the term "heparin" refers to any member of a family of structurally complex, sulphated glycosaminoglycans generally characterized by a structure of repeating glucosamine and glucuronic acid sugar residues (Casu, *Adv. Carbohyd. Chem. and Biochem.* 47: 578–583, 1985). The most widely known heparin is "unfractionated" or "commercial" heparin prepared from bovine lung or porcine gut, which encompasses a heterogeneous mixture of heparin molecules ranging from approximately 8,000 to 20,000 daltons molecular weight (Wolinsky et al., *J. Am. Coll. Cardiol.* 15: 475–481, 1990). However, the term heparin also encompasses a broad range of more homogeneous heparin preparations, as well as heparin-like molecules, including heparan sulfates. Among these particular heparin examples, more specific heparin subtypes are also known. For example, heparan sulfate moieties produced by endothelial cells (Castellot et al., *J. Cell. Biol.* 90: 372–379, 1981) and smooth muscle cells (Fritze et al., *J. Cell. Biol.* 100: 1041–1049, 1985) have been isolated which are reportedly up to 40 times more active than unfractionated heparin for inhibiting proliferation of smooth muscle cells. In addition, among the naturally occurring heparin size variants, fractionated heparin species that exhibit predominantly either anticoagulant or antiproliferative activity have been isolated (Wolinsky et al., *J. Am. Coll. Cardiol.* 15: 475–481, 1990). The latter activity tends to be present in the low molecular weight heparin species, such as heparins in the range of penta- to decasaccharides, which have been reported to also provide greater bioavailability and a longer half-life (Id., Bacher et al., *Thrombosis Res.* 70: 295–306, 1993), and may therefore be particularly useful within specific embodiments of the invention. Also included within the definition of heparin for the purposes of describing the invention are synthetic heparins and heparin derivatives, a variety of which have been produced using conventional chemical synthetic, modifying and degradative techniques (see for example, Roden, L. *The Biochemistry of Glycoproteins and Proteoglycans* (Lennarz, W. J., ed.) pp 267–371, Plenum Publishing Corp., New York, 1980, incorporated herein by reference). The term "low molecular weight heparin having reduced antithrombotic activity" is used to indicate low molecular weight forms having reduced antithrombotic activity (as determined by standard assays) compared to unfractionated heparin.

To determine combinatorially effective doses of antibody and heparin, and/or to evaluate combinatorially effective time periods for separately or sequentially administering anti-PDGF receptor antibody and heparin, the same general methods described above for assaying antihyperplastic activity of anti-PDGF receptor antibodies, and for extrapolating between experimental and clinical applications, are used. These methods include mitogenesis and migration assays using VSMC cell cultures or vascular tissue explants, as well as a variety of in vivo assays which measure the incidence or degree of intimal hyperplasia in a living subject, among others. From these methods, it is either demonstrated or expected that the level of combinatorial inhibition achieved by coordinately administering antibody and heparin varies depending on the respective types and dosages of antibody and heparin used, on the timing and mode of administration of the antibody and heparin, and upon other experimentally and clinically relevant variables, such as the type of cells or tissues treated, or the nature and severity of a blood vessel injury. By adjusting the coordinate administration regimen (eg. heparin and antibody types, dosages, and modes or timing of administration) within the methods of the invention, combinatorial inhibition of intimal hyperplasia can be optimized to facilitate a broad range of specific applications of the invention. For example, different antibody and heparin types and dosages may be desired for different clinical applications. For patients at high risk of thrombosis-related complications, anticoagulant forms of heparin may be clinically desirable. Other patients may be particularly vulnerable to bleeding complications related to the use of anticoagulant forms of heparin, in which case a low molecular weight heparin having reduced antithrombotic activity may be indicated. These and other clinical considerations will be evident to those skilled in the art.

To accomodate the choice of a particular heparin type or dose, the methods of the invention allow for co-variation of the form, timing or dose of antibody to be coordinately administered, such that the administration regimen for the antibody can be coordinately adjusted to maintain a high level of combinatorial inhibition. In other circumstances, the form or dosage of antibody, or the timing or mode of administration of antibody may be imposed by extrinsic circumstances, in which case the heparin administration regimen may need to be coordinately adjusted. For example, in circumstances where a prolonged antibody treatment regimen is desired, lower antibody doses, or less immunogenic antibody forms (e.g., mouse/human chimeric antibodies) may be used to optimize results. In such cases, a coordinate adjustment can be made with respect to the type, dose or timing of administered heparin to achieve a strong, combinatorial antihyperplastic effect.

Using the coordinate antibody and heparin administration methods of the invention, dosages of antibody and heparin in particular may be coordinately varied across a broad range while maintaining a high level of combinatorial inhibition of intimal hyperplasia. This feature of the invention is especially useful for accomodating clinical applications where a low dose of one or the other antihyperplastic agent (i.e. the antibody or heparin) is desired, such as in cases where dose-limiting toxicities, allergies or other complications are present. Within the methods of the invention, coordinately administered anti-PDGF receptor antibodies and heparin have been found to be combinatorially effective in antibody:heparin dose ratios (i.e. ratio of unit antibody dose to unit heparin dose, by weight) ranging between 0.001:1 to 1,000:1, and broader. In other words, a unit dose of antibody as low as $\frac{1}{1,000}$ of a dose of coordinately administered heparin yields a combinatorially inhibitory effect, while antibody doses 1,000 fold greater than a coordinately administered heparin dose also yields a combinatorial effect. This generally inverse-proportional co-variability of antibody and heparin doses provides extreme flexibility for implementing alternative, coordinate administration regimens using the two antihyperplastic agents. At the same time, less extreme co-variation of antibody and heparin doses, embodied in antibody:heparin dose ratios between 0.01:1 and 100:1, and between 0.05:1 and 20:1, also been shown to be combinatorially effective, and are preferably selected in circumstances where moderate to extremely low doses of both the antibody and heparin are clinically desired.

In general, doses of antibody to be coordinately administered with heparin for treating intimal hyperplasia in mammals will be in the range of between approximately 0.1 µg–100 mg of antibody per kilogram of body weight of the mammal per day. Preferably, doses will be between approximately 50 µg–20 mg of antibody per kilogram per day, and more preferably less than 1 mg/kg/day, to conserve expensive antibody stocks and limit side effects while yielding satisfactory levels of inhibition. Generally, doses of heparin will be between approximately 1 µg–100 mg/kg/day. Preferably, heparin doses will be between 20 µg–10 mg/kg/day, and more preferably less than about 1 mg/kg/day. More specifically, coordinately administered doses of antibody and heparin of between approximately 0.5 µg–10 mg/kg/day, and between approximately 1 µg–10 mg/kg/day, respectively, yield strong combinatorially effective results at relatively low doses of both antihyperplastic agents. Where even lower doses of antibody and heparin are desired, coordinately administerd amounts of antibody and heparin of between approximately 5 μg–2 mg/kg/day, and between approximately 50 μg–1 mg/kg/day, respectively, are preferred. Those skilled in the art will recognize that actual doses will be determined with consideration of specific circumstances, including patient parameters and the characteristics of the antibodie(s) (e.g., specificity, specific activity, circulating half-life) and heparin (e.g., antithrombotic activity) administered.

Anti-PDGF receptor antibodies and heparin are preferably administered parenterally, such as by bolus injection or infusion (intravenous, intramuscular, intraperitoneal or subcutaneous) prior to surgery (generally within 24 hours before surgery) and optionally continuing after surgery at intervals of from several hours to several days over the course of one to two weeks or more. Within one embodiment, the antibody is administered as a bolus injection or infusion on the first day of treatment in an amount suficient to provide a minimum circulating level of antibody throughout the intitial, three-day treatment period of between approximately 20 μg and 1 mg/kg body weight. In this regard, it is preferred to use antibodies having a circulating half-life of at least 12 hours, preferably at least 4 days, more preferably up to 14–21 days. Chimeric and humanized antibodies are expected to have circulatory half-lives of up to four days and up to 14–21 days, respectively. In many cases it will be preferable to administer daily doses during a hospital stay, followed by less frequent bolus injections during a period of outpatient treatment. The antibodies and heparin may also be delivered by slow-release delivery systems, including such systems incorporated into vascular grafts or stents, or by way of perfusion or double balloon catheters. Pumps and other known delivery systems may also be employed for continuous infusion. Dosing regimens may be varied to provide the desired circulating levels of antibody and heparin based on the pharmacokinetics of these agents. Thus, doses will be calculated so that the desired circulating levels of therapeutic agents are maintained. Daily doses referred to above may be administered as larger, less frequent bolus administrations to provide the recited dose averaged over the term of administration.

For use within the present invention, anti-PDGF receptor antibodies and heparin are combined or separately formulated into compositions suitable for parenteral (e.g., intravascular, perivascular or transdermal), oral or rectal administration according to conventional procedures and packaged in sterile containers. The antibodies and heparin may be jointly or separately combined with a suitable diluent such as sterile saline or sterile water. The antibody, heparin and antibody/heparin compositions may further contain carriers, stabilizers and excipients such as sugars (e.g. mannitol) or albumin. In the alternative, the antibodies and heparin may be provided in lyophilized or other stable, dry form and reconstituted in a suitable diluent (which may be included with the antibody and heparin) prior to use. These compositions may be packaged in single or multiple dosage form, for example in sealed ampoules or vials. For alternative modes of administration, such as for endovascular administration to inhibit stenosis in vascular grafts, anti-PDGF receptor antibodies and/or heparin may be covalently attached to the graft through their constant regions or incorporated into the graft in slow-release formulations.

The following examples are offered by way of illustration, not by way of limitation.

EXAMPLES

Example 1 discloses the preparation of hybridomas producing monoclonal antibodies to the PDGF receptor alpha and beta polypeptides. Examples 2, 3 and 4 disclose the identification and characterization of anti-PDGF-beta receptor monoclonal antibodies. Example 5 discloses the identification and characterization of anti-PDGF-alpha receptor monoclonal antibodies. Example 6 discloses the determination of the binding specificities of certain representative monoclonal antibodies. Example 7 demonstrates the inhibition of PDGF mitogenic activity on human dermal fibroblasts using anti-PDGF receptor monoclonal antibodies. Example 8 demonstrates the inhibition of PDGF mitogenic activity on baboon smooth muscle cells using anti-PDGF receptor monoclonal antibodies. Examples 9 and 10 disclose the use of anti-PDGF receptor monoclonal antibodies to inhibit baboon serum mitogenic activity. Example 11 demonstrates the inhibition of baboon aortic smooth muscle cell migration by anti-PDGF receptor monoclonal antibodies. Example 12 demonstrates the ability of anti-PDGF receptor MAbs to inhibit PDGF activity up to eight hours after the ligand has bound to receptors. Example 13 discloses the displacement of receptor-bound PDGF from human osteosarcoma cells by anti-PDGF receptor MAbs. Example 14 demonstrates the inhibition of PDGF and baboon serum mitogenic activity on vascular smooth muscle cells using anti-PDGF receptor monoclonal antibodies administered alone or coordinately administered with heparin. Example 15 discloses the use of heparin, alone or coordinately administered with anti-PDGF receptor monoclonal antibodies, to inhibit serum mitogenic activity on baboon vascular smooth muscle cells. Example 16 discloses further studies demonstrating inhibition of serum mitogenic activity on baboon smooth muscle cells using anti-PDGF receptor monoclonal antibodies coordinately administered with heparin. Examples 17 and 18 disclose studies comparing the antimitotic activities of parent murine and mouse/human chimeric anti-PDGF-alpha and beta receptor antibodies coordinately administered with heparin. Example 19 further describes the inhibitory activity of coordinately administered heparin and anti-PDGF receptor antibodies against serum mitogenic activity. Example 20 demonstrates the inhibition of smooth muscle cell outmigration from baboon aortic explants by anti-PDGF receptor monoclonal antibodies ccordinately administered with heparin. Examples 21–23 disclose binding studies of PDGF and anti-PDGF receptor antibodies, in combination and in the presence and absence of heparin, to determine potential binding or activity interactions between PDGF and heparin, and the anti-PDGF receptor antibodies and heparin. Example 24 describes studies to monitor circulating levels of anti-PDGF receptor antibodies following continuous infusion of the antibodies into a baboon, and to measure baboon antibodies generated against the anti-PDGF receptor antibodies. Example 25 discloses studies to determine the in vivo half-life of a chimeric anti-PDGF receptor antibody in a primate model. Example 26 describes a sequential arterial injury model in baboons for testing antihyperplastic agents and treatments following vascular injury. Example 27 describes a baboon model useful in characterizing the role of anti-PDGF receptor antibodies and heparin in inhibiting intimal hyperplasia in primates following acute vascular injury.

Recombinant PDGF AA and BB were produced in yeast essentially as disclosed in U.S. Pat. Nos. 4,889,919; 4,845,075 and 5,037,743, which are incorporated herein by reference in their entirety, and purified to homogeneity from concentrated cell culture media by a combination of cation exchange chromatography, reverse-phase chromatography, gel filtration and $(NH_4)_2SO_4$ fractionation. PDGF AB was prepared from outdated human platelets as disclosed by Hart et al., (*Biochemistry* 29: 166–172, 1991), which is incorporated herein by reference. PDGF-AA, AB and BB were labeled with $^{125}$I by use of Iodobeads™ (Pierce Chemical Co., Rockford, Ill.) as previously described (Hart et al. ibid.) A mutant form of B-chain termed $BB_{tyr}$, which has a tyrosine residue at position 23 of the mature coding sequence in place of phenylalanine, was used for iodination of PDGF-BB. Rabbit anti-mouse IgG and MAb 163.31 were similarly radiolabeled with $^{125}$I using Iodobeads™.

Fusion proteins comprising a human IgG heavy or light-chain joined to the extracellular domain of either the PDGF-alpha receptor or PDGF-beta receptor were prepared essentially as disclosed in U.S. Pat. No. 5,155,027; U.S. patent application Ser. No. 07/634,510 and EP 325,224, which are incorporated herein by reference in their entirety. In one case mouse myeloma cells were transfected with cDNAs for both heavy-chain and light-chain/PDGF receptor extracellular domain fusion proteins. These cells secrete into their culture media a molecule which is analogous to human IgG in that it is composed of two light-chain and 2 heavy-chain fusion proteins. This compound is designated as tetrameric IgG/PDGFr. In another case a cDNA for light-chain/PDGF receptor extracellular domain fusion protein was transfected into the cells alone. These cells secrete monomeric light-chain fusion proteins into their culture media, designated as monomeric IgG/PDGFr. The alpha- and beta-receptor fusion proteins were designated IgG/PDGFr-alpha (tetrameric) and IgG/PDGFr-beta (monomeric and tetrameric), respectively. The fusion proteins were purified by either immunoaffinity purification using anti-PDGF receptor monoclonal antibodies, or by protein A-Sepharose™ chromatography.

Example 1

Preparation of PDGF Receptor Monoclonal Antibodies

Fusion proteins comprising an IgG constant region joined to the extracellular domain of either the PDGF-alpha receptor (PDGFr-alpha) or the PDGF-beta receptor (PDGFr-beta) were prepared essentially as disclosed in U.S. Pat. No. 5,155,027, which is incorporated herein by reference in its entirety. The alpha and beta receptor fusions were designated IgG/PDGFr-alpha and IgG/PDGFr-beta, respectively. The monomeric IgG/PDGFr-beta was expressed as a fusion of a human kappa light chain constant region and the PDGF-beta receptor extracellular domain. The tetrameric IgG/PDGFr-beta was prepared by coexpression of the monomeric construct with a human Ig heavy chain constant region plus hinge sequence fused to the extracellular domain. Alpha receptor fusions were prepared by similar means.

Eight-week-old Balb/c mice were immunized with either purified monomeric or tetrameric IgG/PDGFr-beta or purified tetrameric IgG/PDGFr-alpha. Mice were given intraperitoneal (ip) injections of approximately 10 µg of purified IgG/PDGFr mixed with complete Freund's adjuvant. At approximately 2 week intervals the mice received additional ip injections of IgG/PDGFr-beta or IgG/PDGFr-alpha mixed with incomplete Freund's adjuvant.

Hybridomas were prepared from the immunized mice essentially as disclosed in U.S. Pat. No. 5,094,941, which is incorporated herein by reference in its entirety. Briefly, spleen cells were isolated from the mice and washed. Contaminating red blood cells were removed by lysing with distilled water, and the spleen cells were washed. Any remaining contaminating tissue material was removed by centrifugation.

The NS-1 mouse myeloma cell line (ATCC TIB 18) was used for the fusions. To optimize fusion efficiency, cells were assayed for fusion efficiency, and a clone with a high fusion efficiency was selected. The NS-1 cells were grown in NS-1 media (Table 1) at 37° C., 7% $CO_2$.

Thymocytes obtained from baby mice were used as a feeder layer to condition the culture medium for the cell fusions. Thymus glands were obtained from three- to four-week old Balb/c mice, and thymocytes were isolated as disclosed in U.S. Pat. No. 5,094,941.

NS-1 cells were added to the prepared immunized mouse spleen cells and fusion was carried out essentially as disclosed in U.S. Pat. No. 5,094,941. The cells were cultured in NS-1 medium containing 1×HAT (Table 1) and $2.5×10^6$ thymocytes per ml. The hybridomas were tested between days 9 and 14 for the production of specific antibodies. Cell fusions were designated by number (e.g., 162, 163).

TABLE 1

NS-1 Medium
For a 500 ml solution:

5 ml 10 mM MEM non-essential amino acids (GIBCO BRL, Gaithersburg, MD)
5 ml 100 mM sodium pyruvate (Irvine, Santa Ana, CA)
5 ml 200 mM L-glutamine (GIBCO BRL)
5 ml 100× Penicillin/Streptomycin/Neomycin (GIBCO BRL)
75 ml inactivated fetal calf serum (BioCell, Carson, CA)
1 gm $NaHCO_3$
Add RPMI 1640 (GIBCO BRL) to a total volume of 500 ml. Sterilize by filtration through a 0.22 lm filter.

100× HT Stock 38.5 mg thymidine
136.10 mg hypoxanthine
Dissolve the thymidine and hypoxanthine in distilled $H_2O$ and bring volume up to 100 ml. Warm the solution to 60–70° C. to dissolve the solids. After the solids have dissolved, readjust the volume to 100 ml. Sterilize by filtration through a 0.22 µm filter. Store frozen at –20° C.

1000× A Stock 17.6 ng aminopterin
Add sterile distilled water to the aminopterin and bring the volume to 50 ml. Add 1 N NAOH drop-wise until the aminopterin dissolves. Bring the final volume to 100 ml with distilled $H_2O$. Sterilize by filtration through a 0.22 lm filter. Store frozen at –20° C.

50× HAT 50 ml 100× HT
5 ml 1000× A stock
45 ml distilled $H_2O$
Sterilize the solution by filtration through a 0.22 lm filter. Store frozen at –20° C.

ELISA A Buffer 0.1M $Na_2HCO_3$, pH 9.6
0.02% $NaN_3$

ELISA B Buffer

This buffer may be made with 1% or 2% bovine serum albumin (BSA, available from sigma Chemical Co., St. Louis, MO)

5 or 10 µg BSA (for 1% or 2% BSA, respectively)
250 µl Tween 20 (Sigma)
100 mg $NaN_3$
Add phosphate-buffered saline pH 7.2 (PBS, TABLE 1-continued Sigma) to a final volume of 500 ml.
Alternatively, the buffer may be made up as 1%
or 2% BSA in ELISA C Buffer.

ELISA C Buffer

500 µl Tween 20 (Sigma)
200 mg NaN$_3$
Add PBS to a final volume of 1 liter.

Reaction Buffer 10 ml 0.1M Na-Citrate, pH 5.0
5 mg o-phenylenediamine Dihydrochloride (Sigma)
5 µl H$_2$O$_2$ (Sigma)

Extraction Buffer 100 ml PBS
1.0 ml Nonidet P-40 (NP-40) detergent (Sigma) (1%
final concentration)

Binding Media 500 ml Ham's F-12 (GIBCO BRL)
12 ml 1M Hepes pH 7.4
5 ml 100× Penicillin/Streptomycin/Neomycin (GIBCO BRL)
1 gm rabbit serum albumin (Sigma)

Mito Media
For a 500 ml solution:

250 ml DMEM (GIBCO BRL)
250 ml Ham's F-12 (GIBCO BRL)
0.25 ml 10 mg/ml stock of insulin (GIBCO BRL) to give a
final concentration of 5 µg/ml
1 ml 10 mg/ml stock of transferrin (Collaborative
Research, Bedford, MA) to give a final
concentration of 20 µg/ml
2 ml 4 µg/ml stock of selenium (Aldrich Chemical,
Milwaukee, WI) to give a final concentration of 5
nM
5 ml 10% stock solution of bovine serum albumin
(GIBCO BRL) to give a final concentration of 0.1%.

Example 2

Identification and characterization of Hybridomas
Producing Antibodies to the PDGF Beta Receptor Hybridomas from cell fusion 162 were tested for the production of antibodies to the PDGF-beta receptor. Assays used for identification of positive hybridomas included enzyme linked immunosorbent assays (ELISA), inhibition of $^{125}$I-PDGF-BB binding to IgG/PDGFr-beta, and inhibition of $^{125}$I-PDGF-BB binding to human dermal fibroblasts.

The ELISA assays were carried out in 96-well microtiter plates which had been coated with monomeric IgG/PDGFr-beta. To coat the wells, IgG/PDGFr-beta was diluted to 200 ng/ml in ELISA A buffer (Table 1), and 100 µl of the solution was added to each well. The plates were incubated at 37° C. for 2 hours. After incubation, the plates were washed with ELISA C buffer (Table 1). The plates were then incubated with 150 µl/well of ELISA B buffer (Table 1) at 37° C. to block nonspecific binding sites. The buffer was removed, and the wells were washed with ELISA C buffer.

The test hybridoma supernatants were pooled in groups of two, and 100 µl of the pooled samples was added to each of the microtiter wells. The plates were incubated for 1 hour at 37° C. The plates were washed with ELISA C buffer, then incubated for 1.5 hours at 37° C. with biotin-conjugated rabbit anti-mouse IgG (Vector Labs, Burlingame, Calif.). The wells were washed with ELISA C buffer, then incubated for 30 minutes at 37° C. with 100 µl/well of strepavidin-horseradish peroxidase (Amersham International, Amersham, U.K.). The wells were washed again with ELISA C buffer, then incubated with reaction buffer (Table 1). The reaction was stopped by the addition of 1N H$_2$SO$_4$, and the plates were read in a Dynatech ELISA plate reader (Dynatech Laboratories, Inc. Alexandria, Va.) using a filter to monitor absorbance at 490 nm. Those wells with A490 readings greater than 0.2 were taken as positives. The positive candidates were re-assayed by ELISA as described above to determine the individual culture wells that contained the hybridoma cells producing antibody to IgG/PDGFr-beta.

Hybridomas from cell fusion 162 were also screened for inhibition of $^{125}$I-PDGF-BB binding to IgG/PDGFr-beta. Goat anti-human IgG (Cappel Labs, Malvern, Pa.) was diluted with ELISA A buffer to a final concentration of 2 µg/ml. This mixture was then added to 96-well microtiter plates, 100 µl/well, and the plates were incubated for 1.5 hours at 37° C. The wells were washed with ELISA C buffer, then incubated with 200 µl per well of ELISA B buffer to block nonspecific binding sites. The plates were washed with ELISA C buffer, then incubated for 1.5 hours with tetrameric IgG/PDGFr-beta, and diluted in ELISA B buffer to a final concentration of 25 ng/ml. The wells were washed with ELISA C buffer to remove unbound IgG/PDGFr-beta.

Hybridoma supernatants were pooled in groups of two, and 100 µl of the pooled samples was added to each of the microtiter wells. The wells were incubated for 1 hour at 37° C. To each well was then added 50 µl of $^{125}$I-PDGF-BB (approximately 50,000 cpm per well). After a 1 hour incubation at 37° C. the wells were washed three times with binding media (Table 1). 100 µl of 0.1M NaCitrate, pH 2.5, was added to the wells for 5 minutes at room temperature, the solution was harvested and transfered to 12×75 mm tubes, and the tubes were counted in a gamma counter to determine the level of $^{125}$I-PDGF-BB binding. Antibodies which bound to IgG/PDGFr-beta and blocked $^{125}$I-PDGF-BB binding were detected by a decrease in the level of $^{125}$I-PDGF-BB bound, as compared to culture media alone.

Pools of media that were determined to be positive for IgG/PDGFr-beta neutralizing antibody were rescreened using an assay format similar to that described above to identify the individual wells which contained hybridomas producing the neutralizing antibody.

Media samples from culture wells that were positive either by ELISA or by inhibition of $^{125}$I-PDGF-BB binding were subsequently assayed in a down-regulation assay format (Hart et al., *J. Biol. Chem.* 262: 10780–10785, 1987) for the ability to recognize PDGF-beta receptor on human dermal fibroblasts. The binding of PDGF-BB to the PDGF-beta receptor at 37° C. leads to the internalization of the receptors from the cell surface and a subsequent decrease in the number of cell-surface receptors, a phenomenon refered to as down-regulation. The fibroblasts were plated into 96-well culture dishes at 10,000 cells per well and maintained in culture media for 1–2 days prior to use. To one set of wells was added PDGF-BB at a final concentration of 100 ng/ml on the cells. The cells were incubated for 1.5 hours at 37° C. The culture media was removed from the cells, and the cells were washed with phosphate buffered saline (PBS). Test culture media from the hybridoma cells was then added to duplicate wells of cells that had either received the PDGF-BB treatment or cells that had been left untreated. The cells were subsequently incubated for 2 hours at 4° C., then washed with PBS. 100 µl/well of $^{125}$I-rabbit anti-mouse IgG (100,000 cpm/well) was added to the wells, and the cells were incubated for an additional 1.5 hours at 4° C. The cells were washed with PBS, then incubated for 5 minutes at room temperature with 100 μl/well of extraction buffer (Table 1). The extracts were harvested, transfered to 12×75 mm tubes and counted in a gamma counter to determine the level of $^{125}$I-rabbit anti-mouse IgG binding. If there is antibody in the hybridoma culture supernatants capable of recognizing cell-surface PDGF-beta receptor, then there would be a decrease in the level of $^{125}$I-rabbit anti-mouse IgG binding to those cells that were treated with PDGF-BB to down-regulate the receptors.

Several hybridomas were identified from fusion 162 as making antibody to the PDGF-beta receptor. The hybridomas identified were twice cloned by limiting dilution to obtain individual clones making monoclonal antibody. The clones were screened for antibody production by the assays described above. One hybridoma, named 162.62, was selected for further characterization.

Example 3

Identification and Characterization of Hybridomas Producing Anti-PDGF Beta Receptor Antibodies Hybridomas from cell fusion 163 were tested for the production of antibodies to the PDGF-beta receptor by a combination ELISA/PDGF binding competition assay. These assays were carried out in 96-well microtiter plates. The plates were initially coated with goat anti-human IgG, 2 μg/ml in ELISA A buffer, for 2 hours at 37° C. The plates were washed with ELISA C buffer, then incubated for 1½ hours at 37° C. with ELISA B buffer to block nonspecific binding sites. The plates were washed with ELISA C buffer, then either used immediately or left for 1–4 days at 4° C. until use. At the time of the assay the plates were washed once with ELISA C buffer, then incubated for 1½ hours at 37° C. with tetrameric IgG/PDGFr-beta diluted to 25 ng/ml in binding medium. The plates were then washed with ELISA C buffer to remove unbound IgG/PDGFr-beta.

Hybridoma supernatants were pooled in groups of two wells, and 100 μl of the pooled samples was added to each of the microtiter wells. The plates were incubated for 1 hour at 37° C., then washed with binding medium. To the wells was added horseradish peroxidase-conjugated goat anti-mouse IgG (Tago, Burlingame, Calif.) diluted 1:1000 with binding medium. The wells were incubated for 1 hour at 37° C., then washed with binding medium to remove unbound HRP-conjugated goat anti-mouse IgG. $^{125}$I-PDGF-BB, aproximately 26,000 cpm/well, was then added to the wells for an additional 1 hour at 37° C. The wells were washed with binding medium, then incubated with reaction buffer for development of the ELISA. The reaction was stopped by the addition of 100 μl/well of 1N $H_2SO_4$, and the plates were read in a Dynatech ELISA plate reader using a filter to monitor the absorbance at 490 nm.

The contents of the wells were then transferred to 12×75 mm test tubes, and the samples were counted in a gamma counter to measure the level of $^{125}$I-PDGF-BB binding.

The above-described assay identified hybridoma cultures producing antibody to IgG/PDGFr-beta by ELISA, as well as by the ability to block the binding of $^{125}$I-PDGF-BB to tetrameric IgG/PDGFr-beta. Those pooled samples that were positive were subsequently reassayed using the same protocol as described above to determine the individual culture wells that contained the hybridoma cells producing antibody to IgG/PDGFr-beta.

Individual wells found to be positive for binding to IgG/PDGFr-beta were subseqently assayed for the ability to inhibit $^{125}$I-PDGF-BB binding to human dermal fibroblasts. Human dermal fibroblasts were plated into 24-well culture dishes at approximately 20,000 cells per well. The culture media was removed from the cells, and hybridoma test culture media, 0.5 ml per well, was added to duplicate wells. As a negative control, NS-1 medium alone as added to one set of wells. To a second set of wells was added PDGF-BB at a final concentration of 20 ng/ml in NS-1 medium to determine non-specific binding of $^{125}$I-PDGF-BB. The cells were incubated for 1 hour at 4° C., then $^{125}$I-PDGF-BB, 100 μl/well (approximately 26,000 cpm), was added to each well. The cells were incubated for an additional 1 hour at 4° C., washed with PBS, then incubated with extraction buffer. The extracts were harvested to 12×75 mm tubes and counted in a gamma counter. Test samples that caused a decrease in $^{125}$I-PDGF-BB binding as compared to the NS-1 medium sample were assayed as positive for the ability to inhibit PDGF-BB binding to native PDGF-beta receptor on monolayers of human dermal fibroblasts.

Several hybridomas were identified from fusion 163 to be making antibody to the PDGF-beta receptor. The hybridomas identified were twice cloned by limiting dilution to obtain individual clones making monoclonal antibody. The clones were screened for antibody production by the assays described above. One hybridoma, named 163.31, was selected for further characterization.

Example 4

Characterizaton of Anti-PDGF Beta Receptor MAbs 162.62 and 163.31

MAbs 162.62 and 163.31 (produced from hybridoma clones 162.62 and 163.31, respectively) were compared for the ability to block the binding of $^{125}$I-PDGF-BB to either tetrameric IgG/PDGFr-beta or to PDGF-beta receptor on human dermal fibroblasts. Inhibition of $^{125}$I-PDGF-BB binding to IgG/PDGFr-beta was tested essentially as described above for the intital screening of fusion 163. Instead of adding conditioned culture media, known amounts of antibody diluted in NS-1 medium were added simultaneously with $^{125}$I-PDGF-BB to the IgG/PDGFr-beta coated wells. NS-1 medium alone was used as a negative control. The addition of PDGF-BB, 500 ng/ml, to NS-1 medium was used to determine the level of nonspecific binding by $^{125}$I-PDGF-BB. The wells were incubated at 4° C. for 2½ hours, then washed with PBS. 100 μl of 0.1M citrate pH 2.5 was added to each well to remove the bound $^{125}$I-PDGF-BB, the samples were transferred to 12×75 mm tubes, and the tubes were then counted in a gamma counter.

To assay binding to human dermal fibroblasts, the fibroblasts were plated at approximately 20,000 cells/well in 24-well culture dishes. The cells were used for assay 2–7 days after plating. The antibodies were diluted in binding media to the concentrations shown in Table 2, then mixed with $^{125}$I-PDGF-BB, and 0.5 ml aliquots were added to duplicate wells of fibroblasts. Binding media alone was used as the negative control, and the addition of 500 ng/ml of PDGF-BB was used to determine nonspecific binding for $^{125}$I-PDGF-BB. The cells were incubated for 2½ hours at 4° C., then washed with binding media to remove unbound ligand. The cells were then incubated with extraction buffer, and the extracts were harvested and counted in a gamma counter.

The results of the binding studies are shown in Table 2. The data are presented as specific cpm bound for $^{125}$I-PDGF-BB. Nonspecific binding, determined by the addition of 500 mg/ml of unlabeled PDGF-BB, was 260 cpm for the IgG/PDGFr-beta wells and 105 cpm for the human dermal fibroblasts, and has been subtracted from the data presented. %CB=Percent control binding.

TABLE 2

MAb Inhibition of $^{125}$I-PDGF-BB Binding to IgG/ PDGFr-beta and to Human Dermal Fibroblasts

| MAb | Conc. (µg/ml) | IgG/PDGFr CPM | % CB | Fibroblasts CPM | % CB |
| --- | --- | --- | --- | --- | --- |
| 162.62 | 1.25 | 3 | 0 | 52 | 16 |
|  | 0.62 | 40 | 1 | 71 | 22 |
|  | 0.31 | 71 | 2 | 96 | 30 |
|  | 0.15 | 91 | 3 | 69 | 21 |
| 163.31 | 1.25 | 274 | 9 | 244 | 76 |
|  | 0.62 | 499 | 16 | 372 | 116 |
| Control |  | 3062 | 100 | 322 | 100 |

These results demonstrate that both MAbs 162.62 and 163.31 are potent inhibitors of PDGF-BB binding to IgG/PDGFr-beta. In contrast, MAb 162.62 is a more potent inhibitor than MAb 163.31 for PDGF-BB binding to human dermal fibroblasts.

MAb 162.62 was also analyzed for the ability to displace $^{125}$I-PDGF bound to receptors on monolayers of human dermal fibroblasts. $^{125}$I-PDGF-BB was first incubated with monolayers of human dermal fibroblasts in 24-well culture plates. The cells were washed with PBS, then subsequently incubated for 1 hour at 4° C. with either MAb 162.62, 5 µg/ml, or binding medium alone. The cells were washed, incubated with extraction buffer, and the extracts were counted in a gamma counter to determine the level of $^{125}$I-PDGF-BB binding. To determine nonspecific binding, 500 ng/ml of unlabeled PDGF-BB was added during the first incubation step. The results, presented in Table 3, show that the addition of MAb 162.62 led to a 47% displacement of prebound $^{125}$I-PDGF-BB- Thus, MAb 162.62 was able to displace receptor-bound PDGF-BB from the surface of human dermal fibroblasts.

TABLE 3

Ability of MAb 162.62 to Displace Receptor-bound $^{125}$I-PDGF-BB From Human Dermal Fibroblasts

| 1st Inc. | 2nd Inc. | CPM Bound | BB Removal |
| --- | --- | --- | --- |
| $^{125}$I-BB | Binding Media | 581 |  |
| $^{125}$I-BB | MAb 162.62 | 308 | 47% |

The subclass for MAbs 162.62 and 163.31 were determined by ELISA using IgG/PDGFr-beta coated wells and subclass specific secondary antibody. MAb 162.62 was found to be an IgG2b isotype while MAb 163.31 was found to be an IgG1 isotype.

Example 5

Identification and characterization of Hybridomas Producing Anti-PDGF Alpha Receptor Antibodies Hybridomas from cell fusion 169 were tested for the production of antibodies to the PDGF-alpha receptor by a combination ELISA/PDGF binding competition assay. These assays were carried out in 96-well microtiter plates. The plates were initially coated with goat anti-human IgG, 2 µg/ml in ELISA A buffer, overnight at 4° C. The plates were washed with ELISA C buffer, then incubated with ELISA B buffer to block nonspecific binding sites. The plates were washed with ELISA C buffer, then incubated overnight at 4° C. with tetrameric IgG/PDGFr-alpha diluted to 25 ng/ml in binding medium. The plates were then washed with ELISA C buffer to remove unbound IgG/PDGFr.

Hybridoma supernatants were pooled in groups of two, and 75 µl of the pooled samples was added to each of the microtiter wells. The plates were incubated for 1 hour at 37° C., then washed with ELISA C buffer. To the wells was added horseradish peroxidase-conjugated goat anti-mouse IgG (Tago) diluted 1:1000 with binding medium. The wells were incubated for 1 hour at 37° C., then washed with ELISA C buffer to remove unbound antibody. $^{125}$I-PDGF-AA, approximately 25,000 cpm/well, was then added to the wells for an additional 1 hour at 37° C. The wells were washed with binding medium, then inubated with reaction buffer for development of the ELISA. The reaction was stopped by the addition of 100 µl/well of 1N $H_2SO_4$ and the plates read in a Dynatech ELISA plate reader using a filter to monitor the absorbance at 490 nm.

The contents of the wells were then transfered to 12×75 mm test tubes, and the samples were counted in a gamma counter to measure the level of $^{125}$I-PDGF-AA binding.

This assay identified hybridoma cultures producing antibody to IgG/PDGFr-alpha by ELISA and monitored for antibody which was able to block the binding of $^{125}$I-PDGF-AA to the tetrameric IgG/PDGFr-alpha. Those pooled samples which were positive in the initial assay were reassayed using the same protocol as described above to determine the individual culture wells that contained the hybridoma cells producing antibody for IgG/PDGFr-alpha. Several wells were identified for the presence of antibody directed against IgG/PDGFr-alpha. Of these, two were selected for further analysis, 169.14 and 169.31. Hybridomas from these wells were cloned twice by limiting dilution to obtain single clones producing monoclonal antibody against the PDGF-alpha receptor. The clones were screened using the combination ELISA/$^{125}$I-PDGF-AA binding competition assay essentially as described above.

To verify that MAbs 169.14 and 169.31 recognize native PDGF-alpha receptor on monolayers of mammalian cells, the two antibodies were analyzed for the ability to block $^{125}$I-PDGF-AA binding to alpha T-7 cells. These cells are canine kidney epithelial cells that do not naturally express PDGF-alpha receptor, but have been transfected with a cDNA coding for the full length PDGF-alpha receptor (U.S. Pat. Nos. 5,371,205o. 5,371,205; PCT Publication WO 90/14425). These cells express approximately 100,000 recombinant receptors per cell. The alpha T-7 cells were cultured in 96-well plates to approximately 95% confluency. The culture medium was removed, and dilutions of MAbs 169.14 and 169.31 were added to the cells. Controls were NS-1 medium, and NS-1 medium containing 500 ng/ml of PDGF-BB to determine the nonspecific binding component for $^{125}$I-PDGF-AA- To each well was added 100 µl of the test sample plus 10 µl of $^{125}$I-PDGF-AA (approximately 22,000 cpm per well). The cells were incubated with the samples for 2 hours at 4° C., washed with PBS, then extracted with 100 µl/well of extraction buffer. The extracts were harvested and counted in a gamma counter. The results are shown in Table 4. These results demonstrate that these two MAbs recognize membrane-bound PDGF-alpha receptor in mammalian cells in addition to IgG/PDGFr-alpha.

TABLE 4

Competition for PDGF-alpha Receptor Binding on Alpha T-7 Cells Between Anti-PDGF Alpha Receptor MAbs and $^{125}$I-PDGF-AA

| MAb Conc. (μg/ml) | MAb 169.14 | | MAb 169.31 | |
|---|---|---|---|---|
| | CPM | % CB | CPM | % CB |
| 1.5 | 2 | 1 | 8 | 2 |
| 0.75 | 2 | 1 | 15 | 4 |
| 0.37 | 7 | 2 | 18 | 5 |
| 0.18 | 5 | 2 | 15 | 4 |

CPM = counts per minute of $^{125}$I-PDGF-AA bound in the presence of antibody. The nonspecific value, 28 cpm, which was determined by the addition of 500 ng/ml of PDGF-BB to the wells, has been subtracted from the CPM values given. Control binding was 392 cpm. CB = percent control binding.

The subclass for MAbs 169.14 and 169.31 was determined by ELISA using IgG/PDGFr-alpha coated wells and subclass-specific secondary antibody. Both MAbs 169.14 and 169.31 were assayed positive for IgG2a isotype.

Example 6

Binding Specificity of Anti-PDGF Receptor MAbs

To demonstrate PDGF-receptor subunit binding specificity, MAbs 162.62, 163.31, 169.14 and 169.31 were analyzed for binding to Clone 8 cells and Alpha 1–10 cells. Clone 8 cells are BHK 570 (ATCC CRL 10314) cells that have been transfected with a gene coding for the full length human PDGF-beta receptor (Gronwald et al., Proc. Natl. Acad. Sci. USA 85: 3435–3439, 1988). These cells express approximately 500,000 human PDGF-beta receptors per cell. The Alpha 1–10 cells are BHK 570 cells that have been transfected with a cDNA coding for the full length human PDGF-alpha receptor (U.S. Pat. No. 5,371,205; PCT Publication WO 90/14425). These cells express approximately 1,000,000 human PDGF-alpha receptors per cell. To demonstrate binding specificity for either the PDGF-alpha or beta receptor, cell surface binding studies using the anti-PDGF receptor MAbs were done with these two cell lines.

Figure 2:
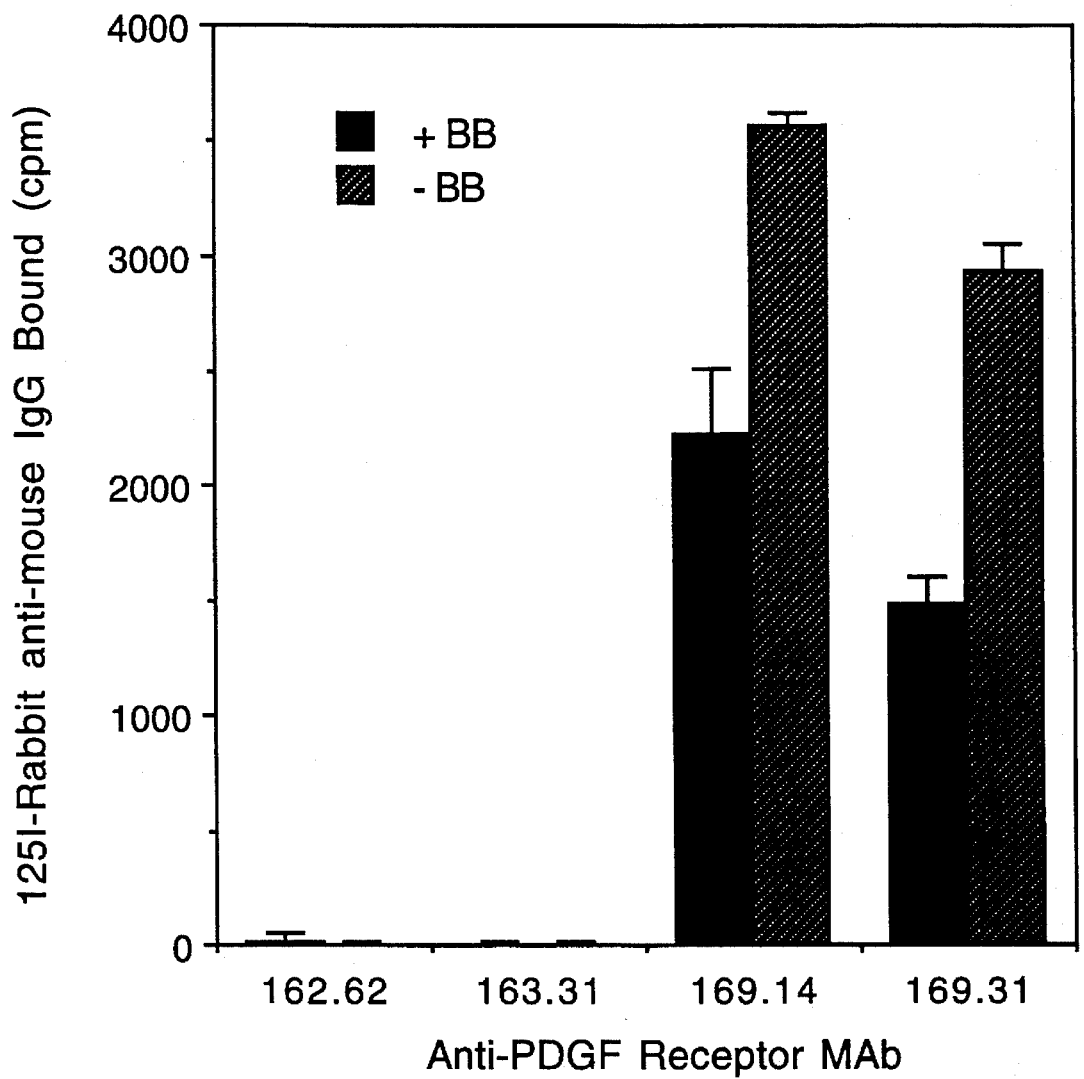
FIG. 2 illustrates the binding of anti-PDGF receptor monoclonal antibodies to cells that express recombinant PDGF-alpha receptor. Results are expressed as mean cpm bound of $^{125}$I-rabbit anti-mouse IgG for triplicate determinations. The bars indicate standard deviation.

Both the Clone 8 and Alpha 1–10 cells were cultured in 24-well plates to confluency. PDGF-BB (200 ng/ml) was added to one-half of the cells to stimulate PDGF receptor down-regulation, and vehicle control (10 mm acetic acid, 0.25% rabbit serum albumin) was added to the other half. The cells were incubated for 1–2 hours at 37° C., then washed with PBS chilled to 4° C. Purified MAbs 162.62, 163.31, 169.14 and 169.31, diluted to 5 μg/ml in binding medium, were added to triplicate wells of the PDGF-BB-treated and nontreated control cells. The cells were incubated for approximately 2 hours on ice, then washed with chilled PBS to remove unbound antibody. The test wells were then incubated on ice for 30 minutes with $^{125}$I-labeled rabbit anti-mouse IgG, diluted in binding medium to approximately 400,000 cpm/well. The wells were washed with PBS, then incubated with extraction buffer. The extracts were harvested and counted in a gamma counter. The results, shown in FIG. 1, demonstrated that only MAbs 162.62 and 163.31 bound specifically to the PDGF-beta receptor, as demonstrated by the significant decrease in binding to the PDGF-BB treated Clone 8 cells when compared to untreated controls. The high level of binding by MAb 169.14 was due to an elevated level of nonspecific binding by this antibody, because there was no significant decrease in $^{125}$I-rabbit anti-mouse IgG binding to the PDGF-BB treated cells. In contrast, only MAbs 169.14 and 169.31 showed binding to the PDGF-alpha receptor as demonstrated by the specific binding to the Alpha 1–10 cells (FIG. 2). Due to the ability of the antibodies to bind to cell surface PDGF receptor, these results confirm that these antibodies recogonize extracellular epitopes on the PDGF receptors.

Example 7

Neutralization of PDGF Mitoqenic Activity on Human Dermal Fibroblasts

Figure 3A:
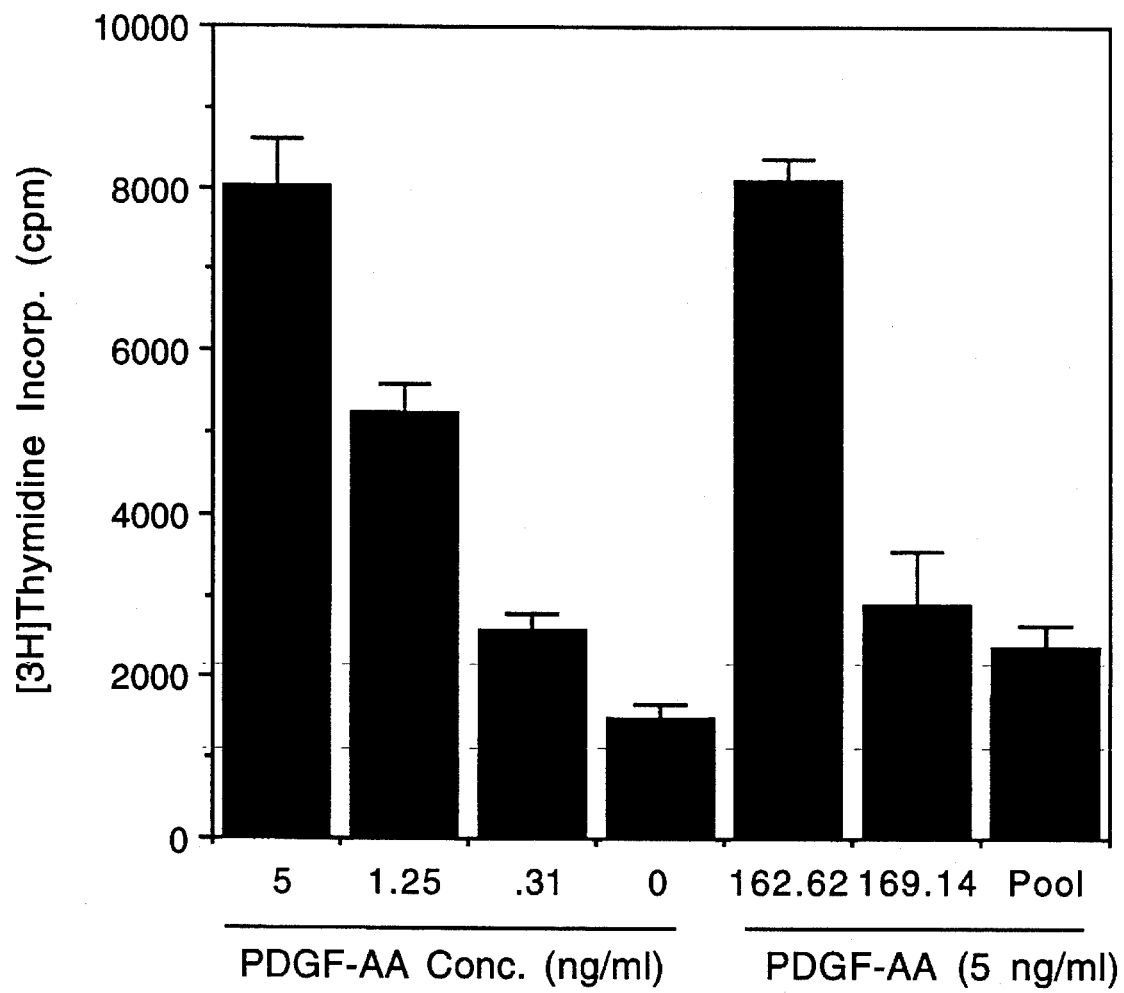
FIGS. 3A–3C illustrate the inhibition of PDGF mitogenic activity on human dermal fibroblasts by anti-PDGF receptor monoclonal antibodies. The results are presented as the mean level of [$^3$H]thymidine incorporation for each of the PDGF ligand test conditions. Standard deviation is shown by the T at the top of each bar. Each panel also shows a standard curve for PDGF ligand alone. A) PDGF-AA stimulation, B) PDGF-AB stimulation, C) PDGF-BB stimulation.
Figure 3B:
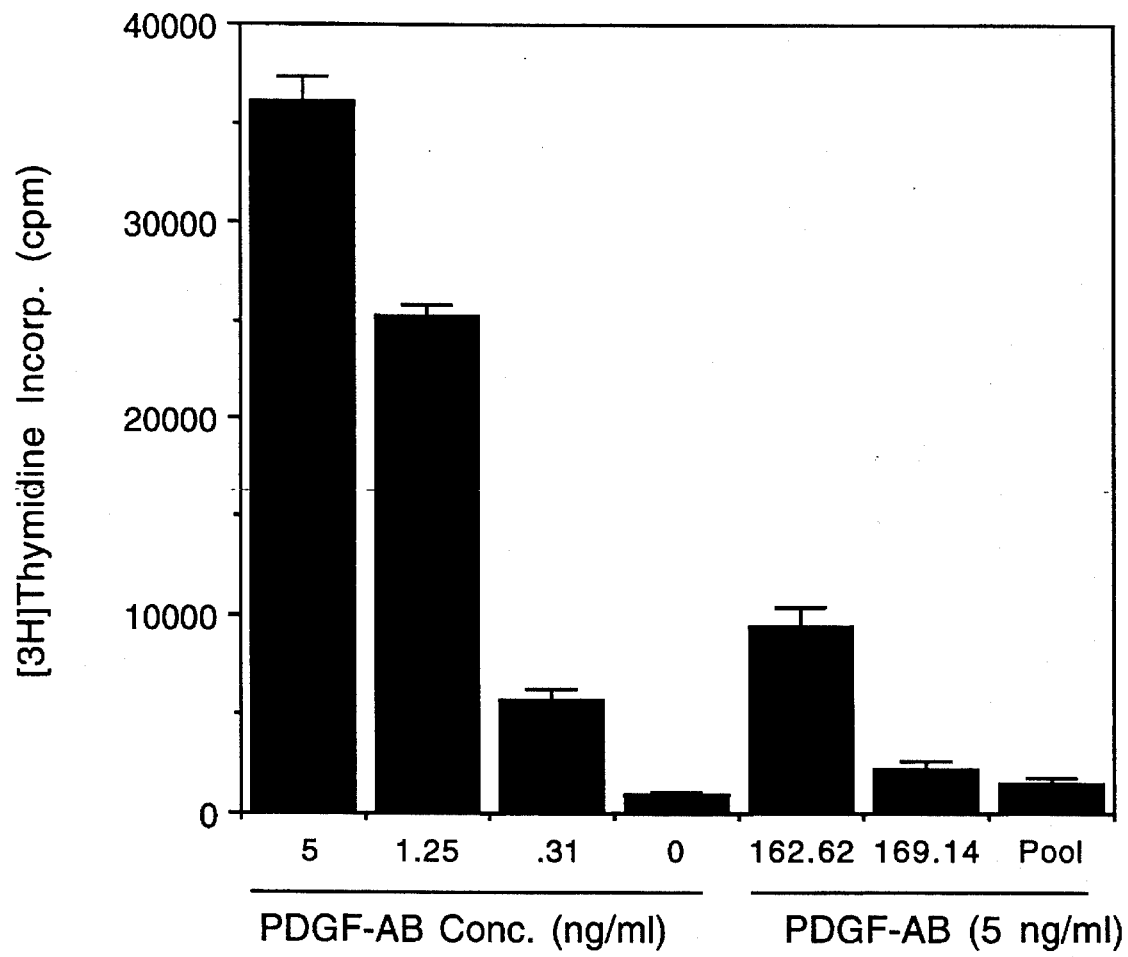
Figure 3C:
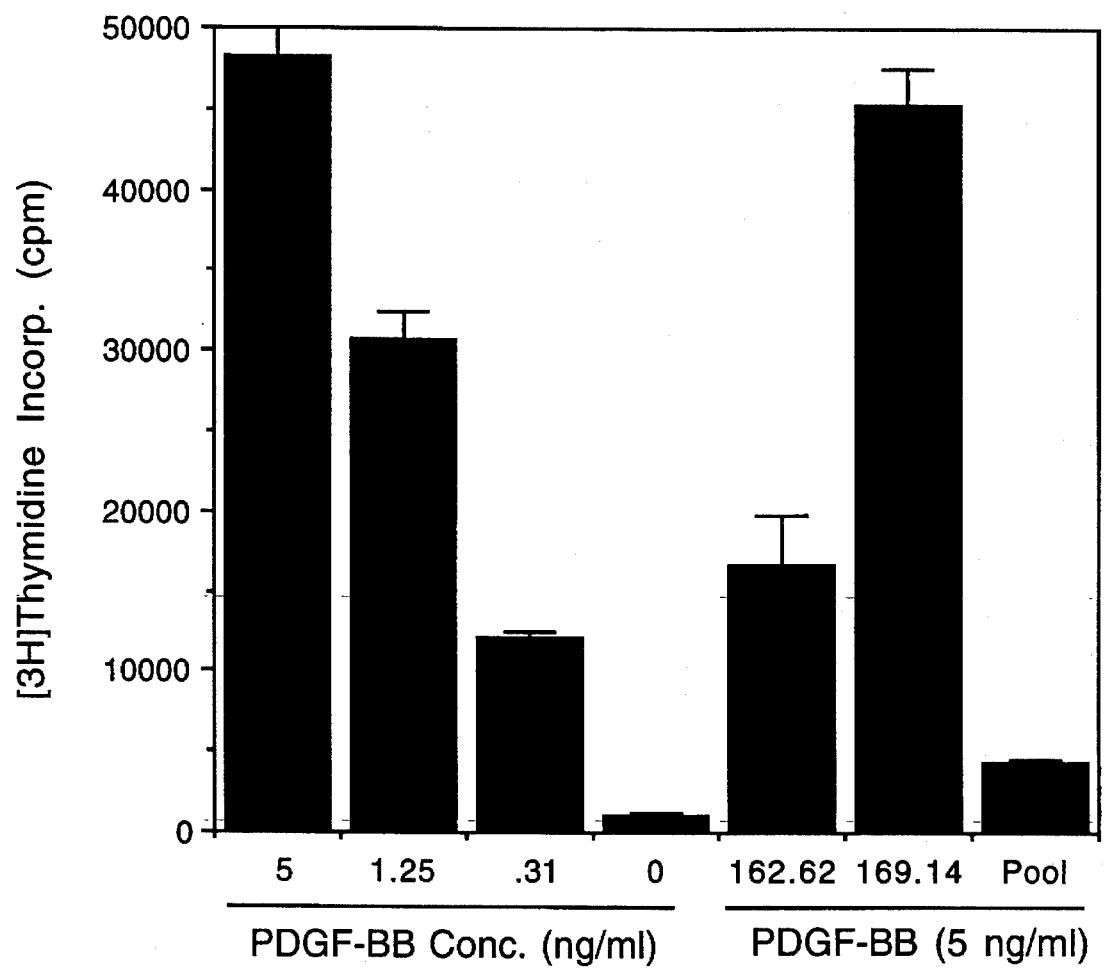

Human dermal fibroblasts were plated at approximately 20,000 cells per well in 24-well culture dishes and grown until quiescent in DMEM (GIBCO BRL) containing 2% fetal calf serum. The cells were stimulated with either PDGF-AA, AB or BB. Standard curves were run with concentrations of 5, 1.25, 0.31 and 0 ng/ml final concentration on the cells. Stock PDGF dilutions were made with 10 mM acetic acid containing 0.25% rabbit serum albumin, and, 50 μl of the stock samples, or vehicle alone, was added to the culture wells to give the desired final concentrations. To analyze the ability of MAbs 162.62 and 169.14 to neutralize the mitogenic activity of each of the three PDGF ligands, 5 ng/ml of PDGF was added to wells along with 20 μg/ml (final concentration on the cells) of MAbs 162.62 and 169.14 alone, or 20 μg/ml of a pool of the two antibodies. The cells were incubated with the test samples for approximately 20 hours at 37° C. The media was aspirated, then replaced with 1 ml of DMEM containing 5% fetal calf serum and supplemented with 1 μCi/ml of [$^3$H]thymidine. The cells were incubated for 4 hours at 37° C., washed with PBS, then harvested with trypsin and counted for [$^3$H]thymidine incorporation in a Wallac (Turku, Finland) Betaplate™ liquid scintillation counter. The results, presented in FIG. 3A, demonstrate that PDGF-AA mitogenic activity was inhibited by MAb 169.14 as well as by the antibody pool, but not by MAb 162.62. Mitogenic activity of PDGF-AB was inhibited approximately 80% by MAb 162.62, and greater than 92% by MAb 169.14 or the antibody pool (FIG. 3B). In contrast, activity of PDGF-BB was only minimally inhibited by MAb 169.14, but was inhibited approximately 80% by MAb 162.62 and greater than 92% by the antibody pool (FIG. 3C).

These results are consistent with the model of PDGF ligand binding which describes that PDGF-AA binds to PDGF-alpha/alpha receptor dimers, PDGF-AB binds to PDGF-alpha/alpha and -alpha/beta receptor dimers and PDGF-BB binds to all three PDGF receptor dimers; -alpha/alpha, -alpha/beta and -beta/beta (reviewed in Hart et al., J. Invest. Derm. 94: 535–575, 1990). Thus, if MAb 169.14 binds to and inhibits PDGF binding to the alpha receptor, then it would be expected to inhibit essentially 100% of PDGF-AA and AB mitogenic activity, since alpha receptor binding is required for both of these ligands. This model is consistent with the results described above. The binding to and the inhibition of the PDGF-beta receptor by MAb 162.62 would then be expected to limit the amount of PDGF-AB and BB mitogenic to a level that is consistent with PDGF-AA, since AB and BB would only be able to bind to alpha/alpha dimers. Again, this is consistent with the findings of the study descibed above.

In summary, anti-PDGF-receptor MAbs 162.62 and 169.14 are able to inhibit the mitogenic activity of the three forms of PDGF in manners that are consistent with the current hypothesis as to PDGF receptor binding by the three PDGF ligands. Additionally, the use of the two antibodies in conjunction is able to inhibit essentially 100% of the PDGF mitogenic activity on human dermal fibroblasts.

Example 8

Inhibition of PDGF Mitogenic Activity on Baboon Smooth Muscle Cells

Anti-PDGF receptor MAbs were analyzed for the ability to inhibit the mitogenic activity of PDGF on baboon smooth muscle cells. All mitogenesis assays performed on baboon vascular smooth muscle cells (BVSMCs) were done on primary cultures of cells between passages 3 and 7 in culture. The initial cultures were established from outgrowth of aortic tissue explants. Baboon smooth muscle cells were plated at approximately 30,000 cells per well, in DMEM supplemented with 10% fetal calf serum, into 24-well culture dishes. Two days prior to use the culture media was removed, and 1 ml of Mito Media (Table 1) was added to each well to allow the cells to become quiescent. At the time of the experiment the cells were stimulated with either PDGF-AA, AB or BB. Standard curves were run for each of the three ligands using final concentrations shown in FIGS. 4–6. 20× stock solutions were made for each of the PDGF concentrations by dilution in 10 mM acetic acid containing 0.25% albumin, and 50 μl of PDGF or dilution vehicle alone was added to the culture wells.

Figure 4:
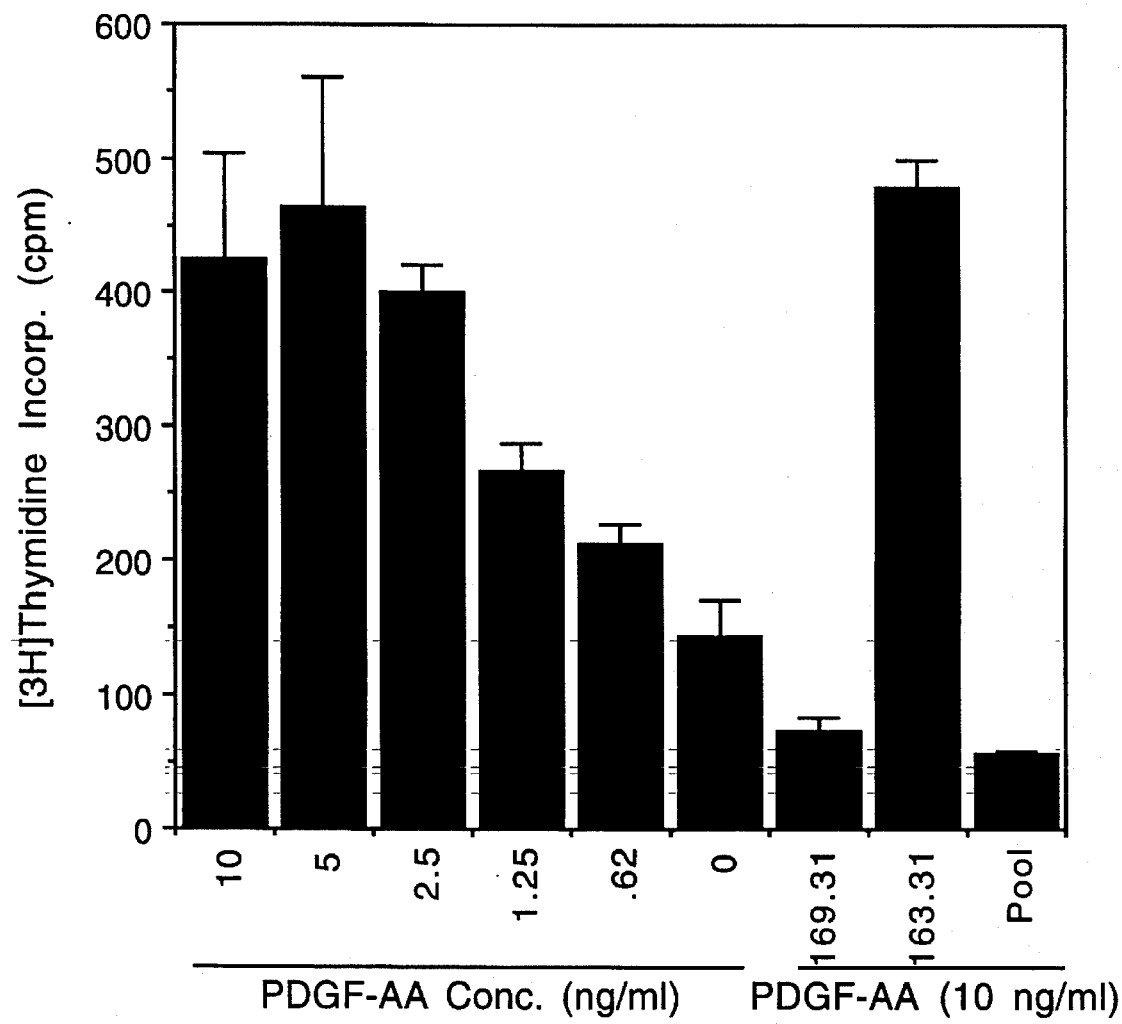
FIG. 4 illustrates the inhibition of PDGF-AA mitogenic activity on baboon smooth muscle cells by anti-PDGF receptor monoclonal antibodies. A standard curve for ligand alone is shown on the left. Results are presented as the mean level of [$^3$H] thymidine incorporation. Standard deviation is shown by the T at the top of each bar.
Figure 5:
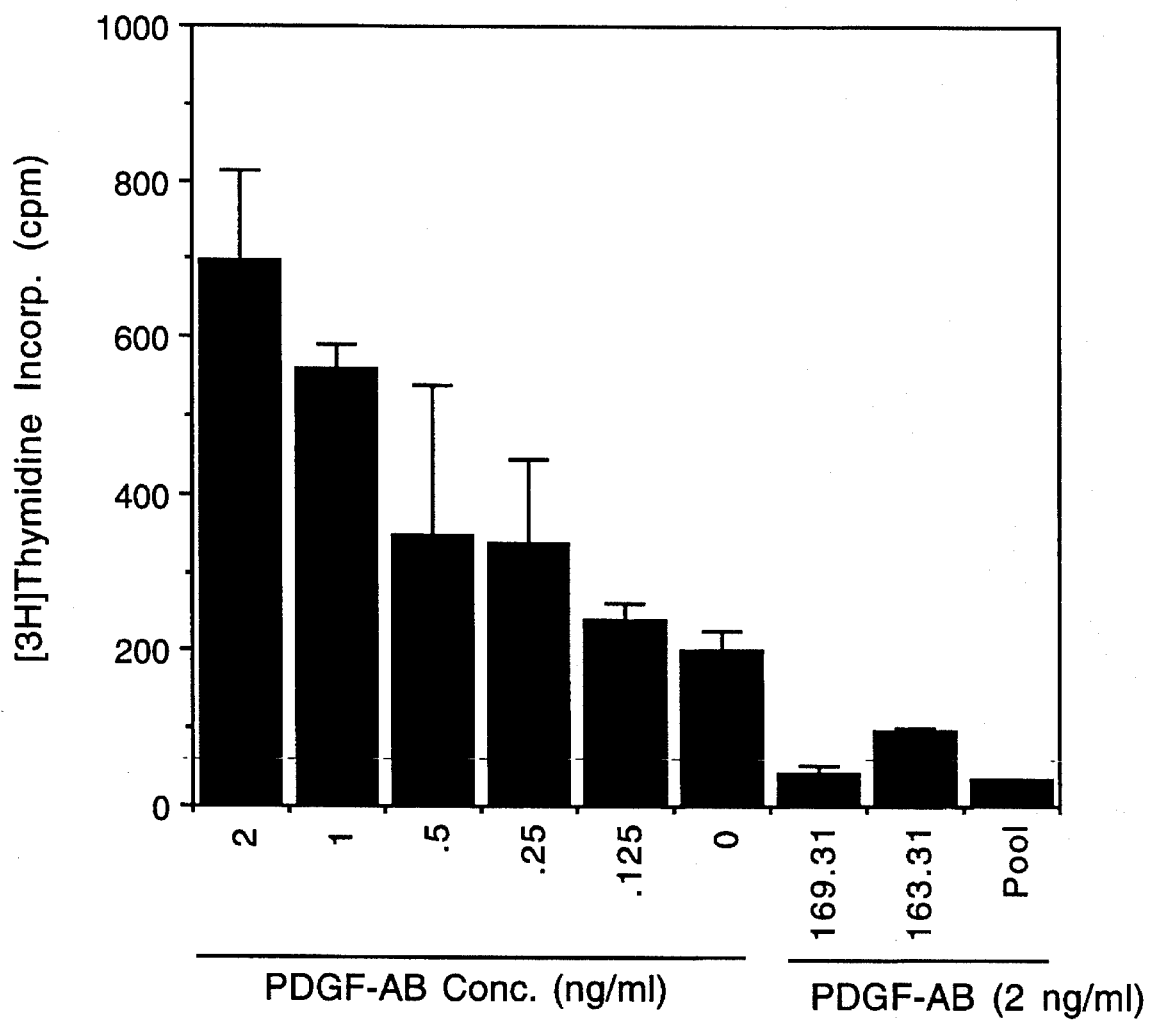
FIG. 5 illustrates the inhibition of PDGF-AB mitogenic activity on baboon smooth muscle cells by anti-PDGF receptor monoclonal antibodies. A standard curve for ligand alone is shown on the left. Results are presented as in FIG. 4.
Figure 6:
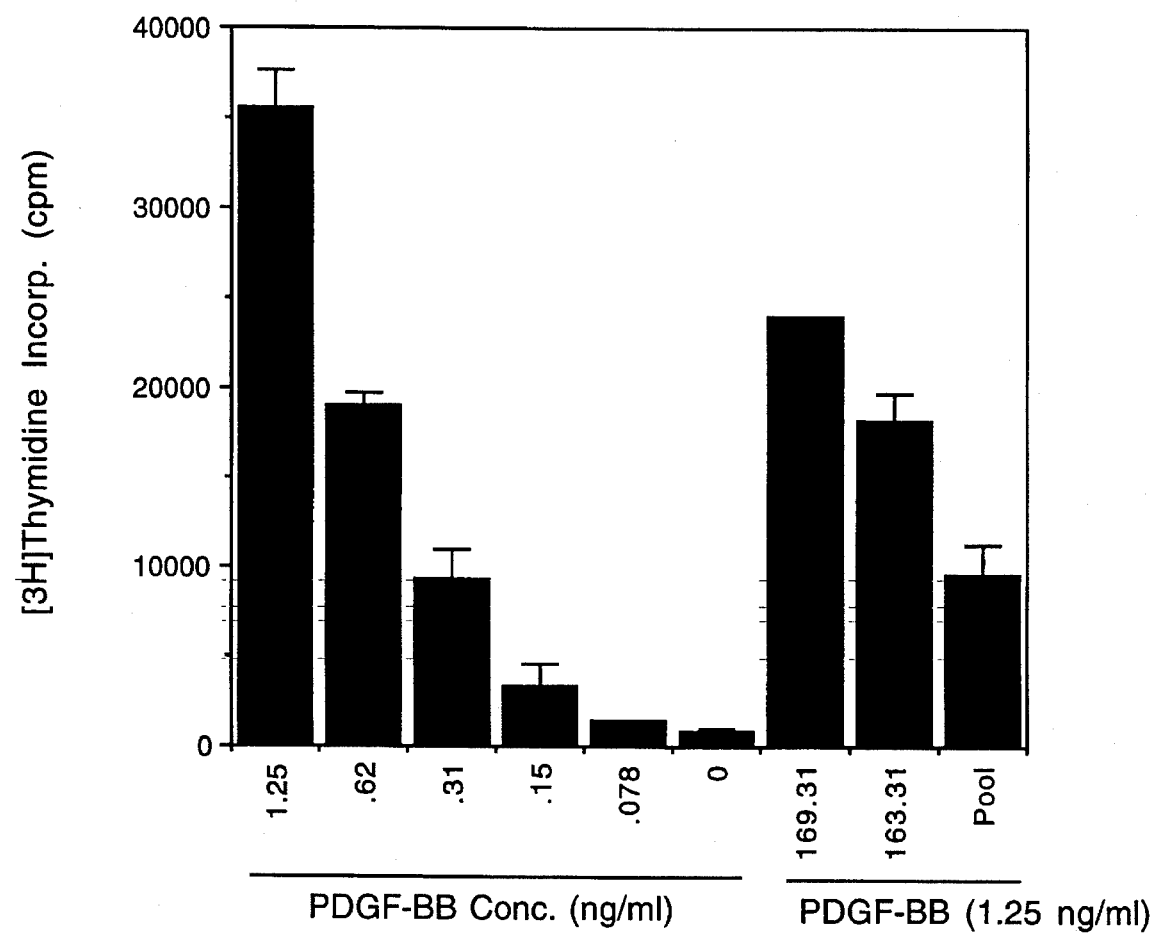
FIG. 6 illustrates the inhibition of PDGF-BB mitogenic activity on baboon smooth muscle cells by anti-PDGF receptor monoclonal antibodies. A standard curve for ligand alone is shown on the left. Results are presented as in FIG. 4.

For the mitogenesis assays, final PDGF concentrations of 10, 2 and 1.25 ng/ml were used for PDGF-AA, AB and BB, respectively. MAbs 163.31 and 169.31 were added to the PDGF-containing wells at a final concentration of 25 μg/ml. For pools of the two antibodies, the final concentration of antibody on the cells was 25 μg/ml total, or 12.5 μg/ml for each of the MAbs. The cells were incubated between 20–24 hours at 37° C. For the PDGF-AA and AB studies, 50 μl of a 40 μCi/ml solution of [$^3$H]thymidine was added to each well. For the PDGF-BB study the media was aspirated, then replaced with 0.5 ml of DMEM containing 5% fetal calf serum and supplemented with 2 μCi/ml of [$^3$H]thymidine. The cells were incubated between 2–4 hours at 37° C., washed with PBS, then harvested with trypsin and counted for [$^3$H]thymidine incorporation in a Betaplate™ liquid scintillation counter (Wallac). As shown in FIG. 4, PDGF-AA mitogenic activity was 100% inhibited by MAb 169.31 as well as by the antibody pool, but not by MAb 163.31. PDGF-AB mitogenic activity was completely inhibited by both MAbs individually as well as by the antibody pool (FIG. 5). It is interesting to note that the level of [$^3$H] thymidine incorporation in the presence of the MAbs was below the level obtained with the addition of vehicle control only. This was similarly seen with MAb 169.31 on the PDGF-AA plate (FIG. 4). For the PDGF-BB stimulated cells, MAb 169.31 and MAb 163.31 gave less than 50% inhibition individually, while a pool of the two antibodies was able to inhibit approximately 75% of the PDGF mitogenic activity (FIG. 6).

Figure 7A:
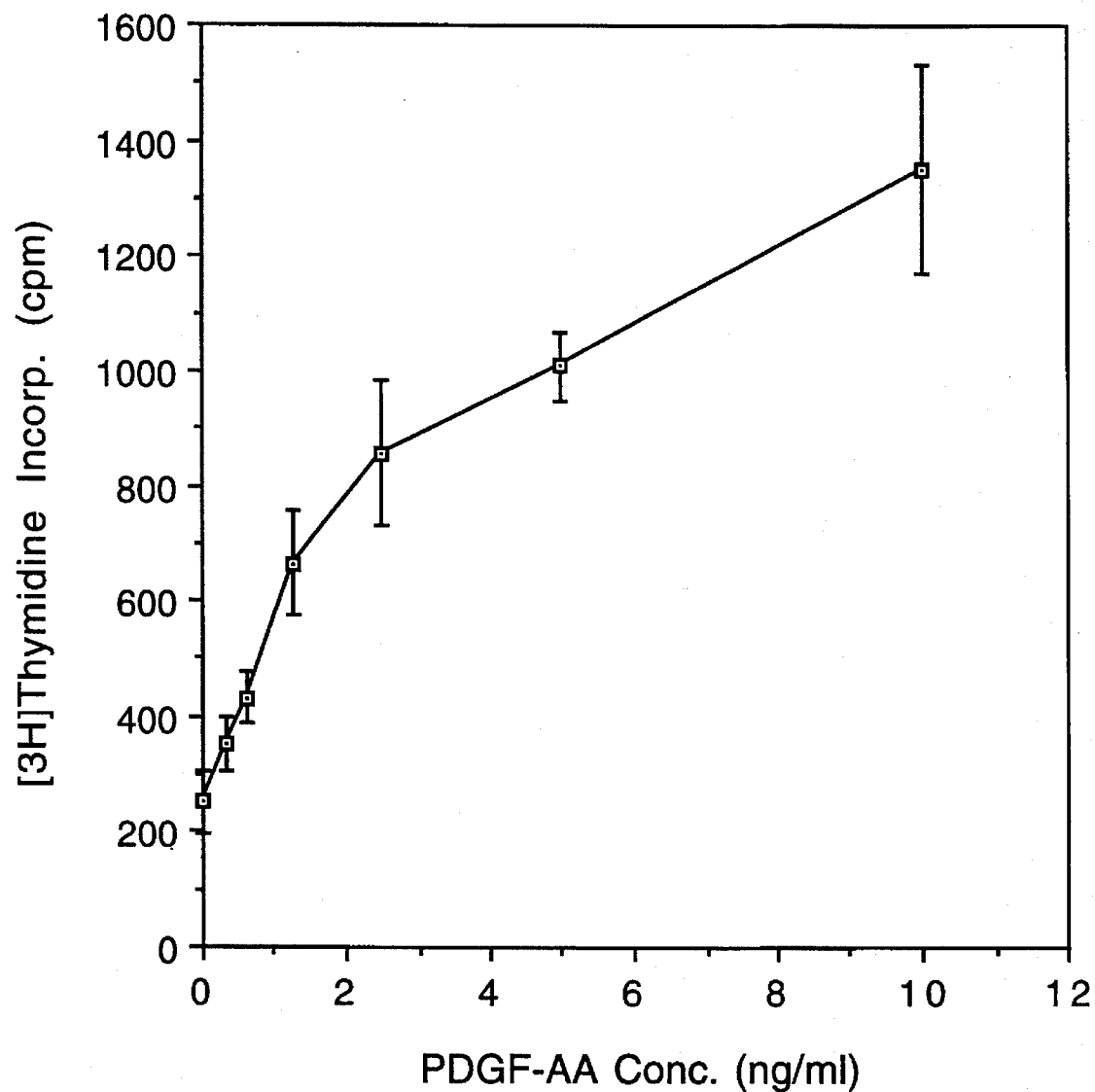
FIGS. 7 A and B illustrate titration of representative monoclonal antibodies to inhibit the mitogenic activity of PDGF-AA on baboon smooth muscle cells. The results are presented as the mean level of [$^3$H] thymidine incorporation for each of the PDGF-AA test conditions. Standard deviation is shown by the T for the PDGF-AA standard curve samples. (A) Standard curve of PDGF-AA mitogenic activity. (B) Inhibitory potency of MAbs 169.14 and 169.31 for PDGF-AA mitogenic activity as shown by a decrease in the level of [$^3$H] thymidine incorporation.
Figure 7B:
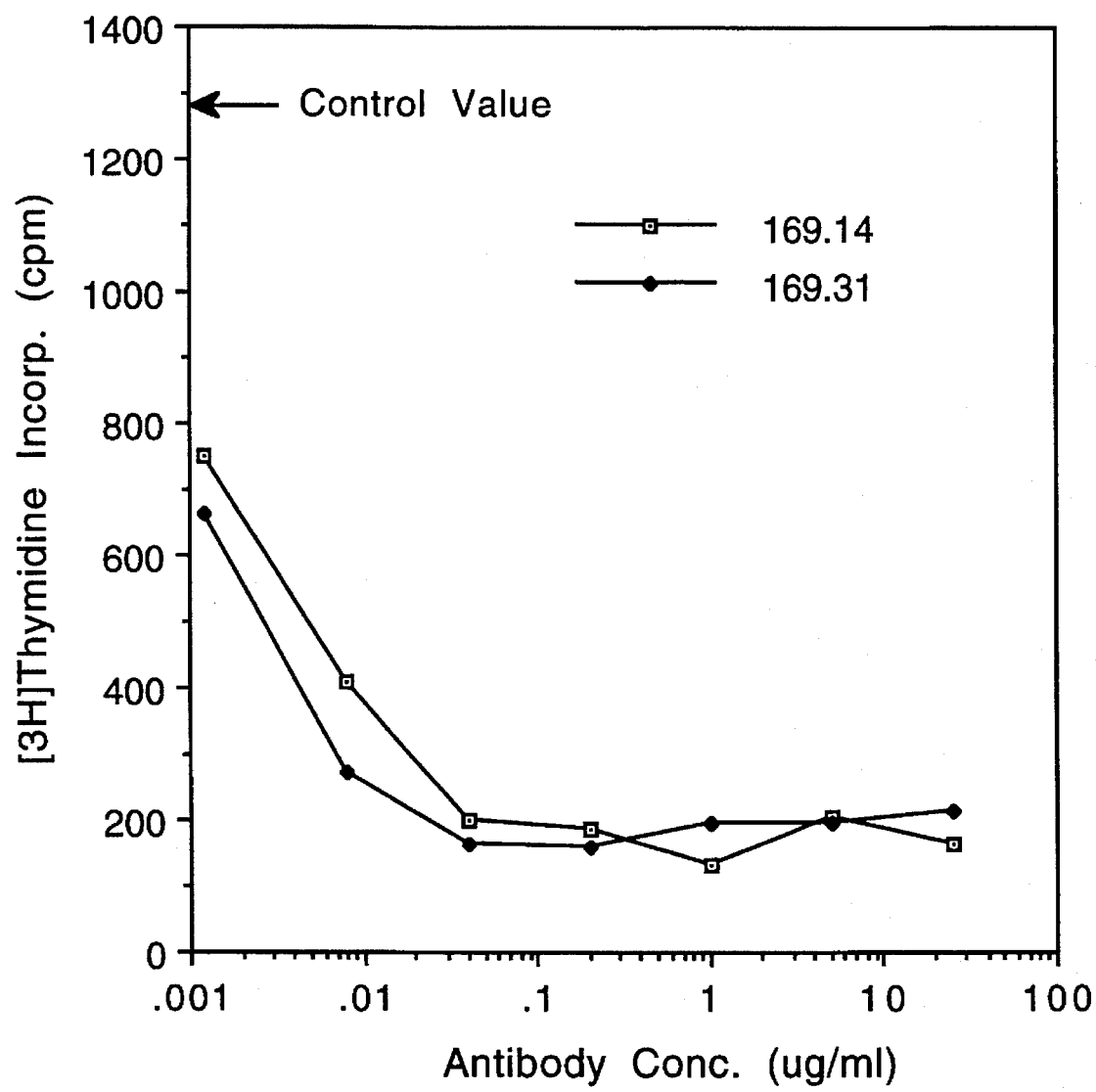

To further demonstrate the inhibitory potency of these antibodies to neutralize the mitogenic activity of PDGF on baboon smooth muscle cells, two anti-PDGF-alpha receptor MAbs, 169.14 and 169.31, were analyzed for the ability to inhibit PDGF-AA mitogenic activity. BVSMCs were plated and treated essentially as described above. To one set of wells were added increasing concentrations of PDGF-AA in order to generate a standard curve of PDGF-AA mitogenic activity (FIG. 7A). The PDGF-AA samples ranged from 10 ng/ml down to 0.31 ng/ml. To a second set of wells, a standard dilution of PDGF-AA was added to give a final concentration of 10 ng/ml. Decreasing concentrations of MAbs 169.14 and 169.31 were then added to the wells to monitor the inhibitory potency for each of the MAbs, as determined by a decrease in the level of [$^3$H]thymidine incorporation (FIG. 7B). The findings demonstrate that even at 8 ng/ml of antibody, there was greater than 90% inhibition of a 10 ng/ml solution of PDGF-AA.

Example 9

Inhibition of Baboon Serum Mitogenic Activity on Baboon Smooth Muscle Cells

Anti-PDGF receptor MAbs were analyzed for the ability to inhibit the mitogenic activity of baboon serum on baboon smooth muscle cells. BVSMCs were plated at approximately 30,000 cells per well, in DMEM supplemented with 10% fetal calf serum, into 24-well culture dishes. Three days prior to use the culture media was removed, and 1 ml of Mito Media (Table 1) was added to each well to allow the cells to become quiescent. At the time of the experiment the cells were stimulated with varying amounts of baboon serum.

A standard curve was generated for the serum sample. 20× stock solutions were made for each of the serum concentrations, and 50 μl of the serum dilution or dilution vehicle, PBS, was added to the culture wells to give final serum concentrations on the cells ranging from 2.5% down to 0.15%. MAbs 169.31 and 163.31 were analyzed for the ability to inhibit baboon serum mitogenic activity. A final serum concentration of 2.5% was used for the antibody inhibition studies. MAbs 169.31 and 163.31 were added to the serum-containing wells at a final concentration of 25 μg/ml. For pools of the two antibodies, the final concentration of antibody on the cells was 25 μg/ml total, or 12.5 μg/ml for each of the MAbs. The cells were incubated with the serum samples for approximately 20 hours at 37° C. At that time the media was aspirated from the cells, then replaced with 0.5 ml of DMEM containing 5% fetal calf serum and supplemented with 2 μCi/ml of [$^3$H]thymidine. The cells were incubated for approximately 3 hours at 37° C., washed with PBS, then harvested with trypsin and counted for [$^3$H]thymidine incorporation in a Betaplate™ liquid scintillation counter (Wallac). The results, presented in FIG. 8, demonstrate that baboon serum mitogenic activity is minimally inhibited by MAb 169.31, but inhibited greater than 50% by MAb 163.31. The pool of the two antibodies inhibited greater than 75% of the serum mitogenic activity.

These results demonstrate that the majority of the mitogenic activity in baboon serum towards baboon smooth muscle cells can be inhibited through the use of anti-PDGF receptor monoclonal antibodies. Studies by the inventors have shown that the predominant form of PDGF in baboon platelets is PDGF-BB. Due to the large percentage of PDGF-beta receptors on baboon smooth muscle cells, it is consistent that the anti-PDGF-beta receptor MAb would have the largest inhibitory activity towards baboon serum.

Example 10

The Effect of Circulating MAb 169.31 on Baboon Serum Mitogenic Activity

A study was performed to monitor the circulating levels of MAb 169.31 after the administration of a bolus intravenous (i.v.) injection of 25 mg into a baboon. Serum was obtained at various intervals following antibody injection, and the level of circulating antibody was determined by ELISA.

Sheep anti-mouse IgG was added to 96-well microtiter dishes in ELISA buffer A at a concentration of 2 µg/ml. The plates were incubated overnight at 4° C., washed with ELISA C buffer, then incubated with ELISA B buffer to block nonspecific binding sites. The plates were washed with ELISA C buffer, then incubated with 100 µl/well of test sample. Baboon plasma or serum containing monoclonal antibody 169.31 was diluted 1:1000 with ELISA B buffer and added to the test wells. Standards, consisting of purified MAb 169.31 spiked into control baboon plasma or serum, were diluted 1:1000, similar to the test plasma/serum samples, then added to the test wells. Standards ranged from 100 ng/ml to 1.56 ng/ml final concentration in the test wells. The plasma/serum samples were incubated in the wells for 1–2 hours at 37° C. the wells washed with ELISA C buffer, then goat anti-mouse IgG conjugated with horseradish peroxidase was added. The wells were incubated for 1 hour at 37° C. washed with ELISA C buffer, then incubated with Reaction buffer. The reaction was stopped by the addition of 1N $H_2SO_4$, and the plates were read in an ELISA plate reader at 490 nm. ELISA analysis of the baboon serum samples for circulating levels of MAb 169.31 indicated that the in vivo half-life of this murine antibody was approximately 15 hours.

In addition, the relative mitogenic potency of the serum samples obtained at 1 hour and 18 hours following the injection was determined. At thess times the circulating levels of antibody in the baboon were determined to be 46 µg/ml and 21 µg/ml, respectively. The 1 hour and 18 hour serum samples were then compared to a control serum sample for relative mitogenic activity. Dilutions of the serum samples were added to baboon vascular smooth muscle cells that had been cultured essentially as described in the baboon serum study presented above. The final serum concentrations on the smooth muscle cells ranged from 1.25% down to 0.15%. The baboon smooth muscle cells were monitored for the level of [$^3$H] thymidine incorporation, as a means to determine mitogenic activity, essentially as described above.

Figure 8:
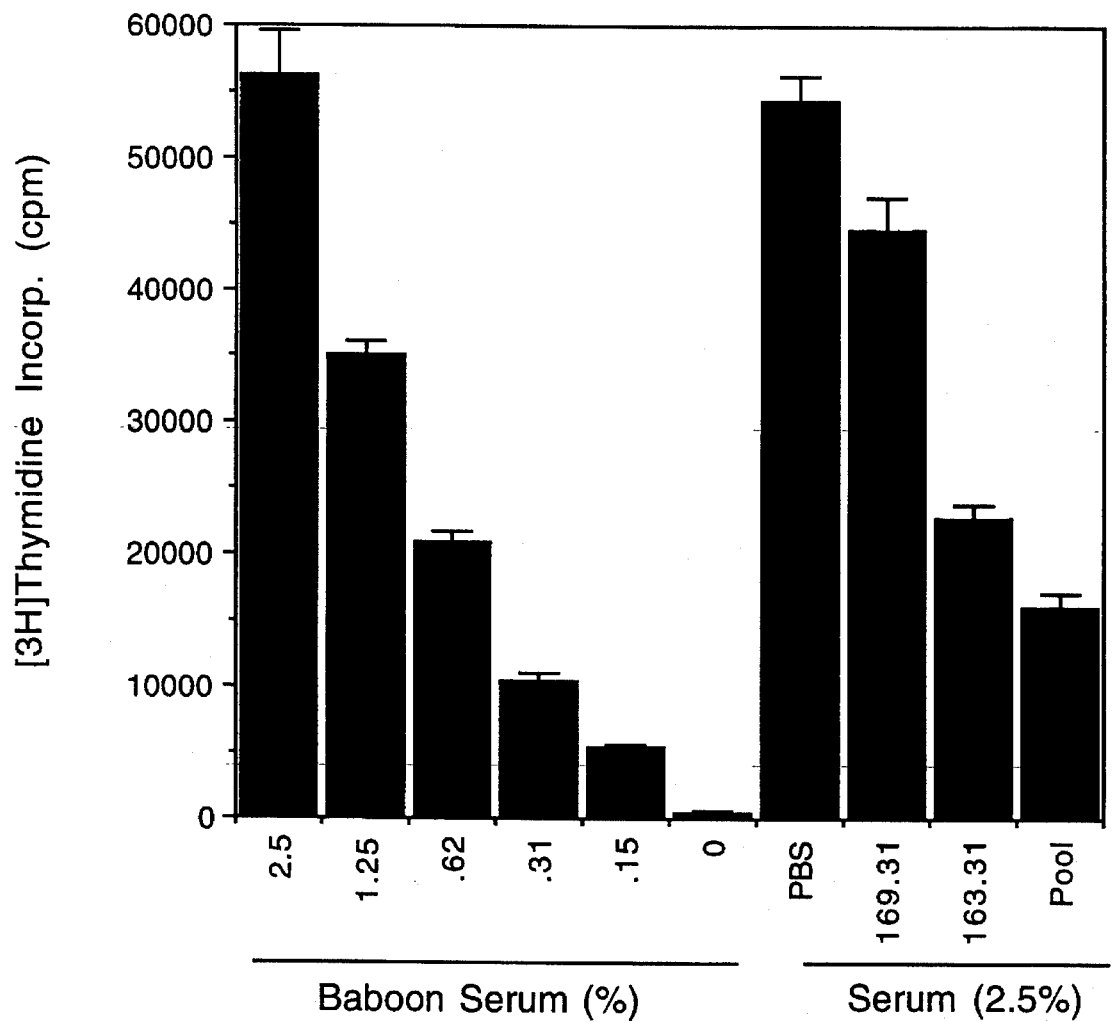
FIG. 8 illustrates the inhibition of baboon serum mitogenic activity on baboon smooth muscle cells by anti-PDGF receptor monoclonal antibodies. A standard curve for serum alone is shown on the left. The results are presented as the mean level of [$^3$H] thymidine incorporation. Standard deviation is shown by the T at the top of each bar.
Figure 9:
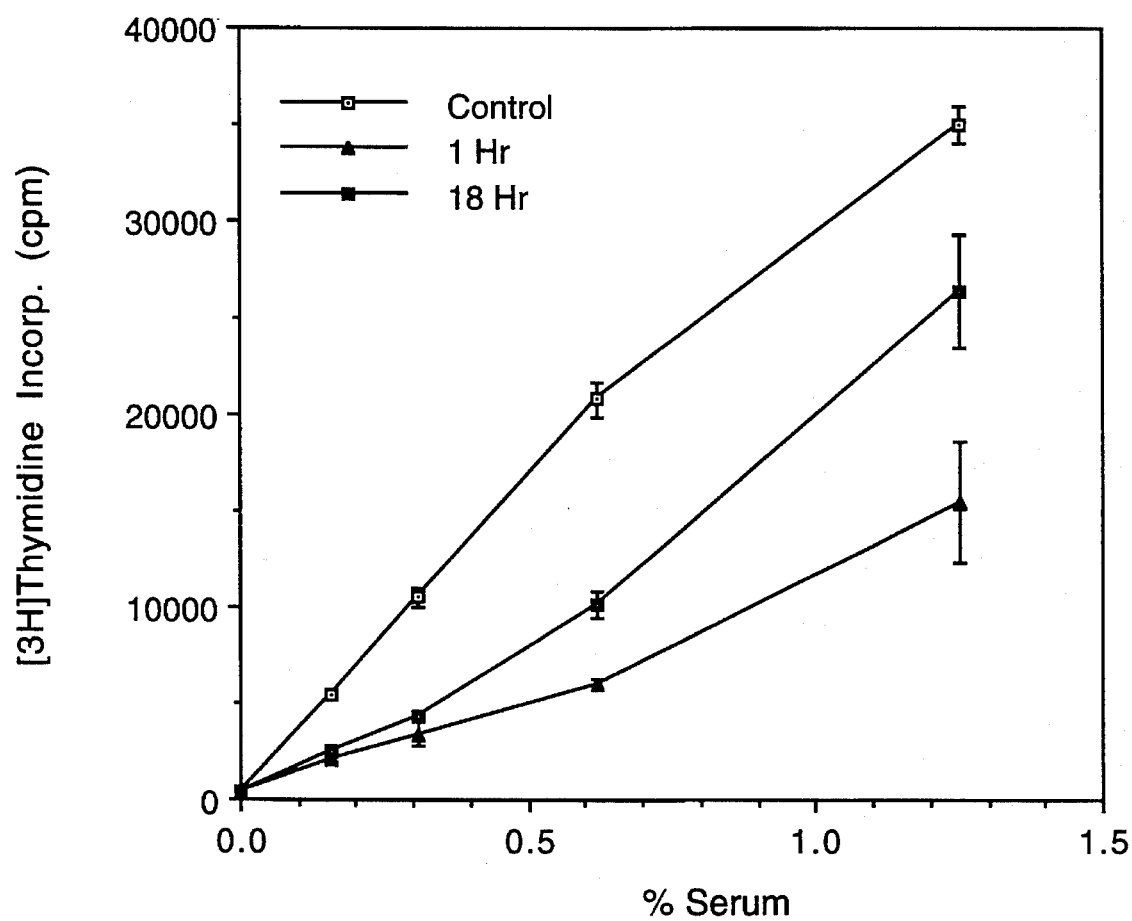
FIG. 9 illustrates the mitogenic activity of baboon serum, in the presence of anti-PDGF alpha receptor monoclonal antibody 169.31, on baboon smooth muscle cells.

The results, presented in FIG. 9, show that there was a significant decrease in the relative mitogenic potency for both the 1-hour and 18-hour serum samples as compared to the control sample, with the 18-hour sample being intermediate in mitogenic activity between the control and 1-hour samples. The level of neutralization by MAb 169.31 that was present in the 18-hour serum sample is consistent with the level of neutralization obtained when this antibody was added ex vivo to control baboon serum (FIG. 8). Thus, these results demonstrate that MAb 169.31 circulating for at least 18 hours in baboon blood retains essentially all of its biological activity for inhibiting baboon serum mitogenic activity on baboon smooth muscle cells.

Example 11

Inhibition of Cell Outgrowth from Baboon Aortic Explants

Anti-PDGF receptor monoclonal antibodies were tested for the ability to decrease the rate of smooth muscle cell outmigration from explants of baboon aortic tissue. The inner media of the thoracic aorta of baboons was dissected out in DMEM culture media containing 10 mM Hepes. The aortic tissue was sectioned into 1 mm square sections, and the explants were placed onto tissue culture flasks. After a 10 minute incubation to allow time for the explants to adhere to the flasks, culture media, DMEM plus 6 µg/ml insulin and 5 µg/ml transferin, was added to the explants, and the samples were incubated at 37° C. with 5% $CO_2$. A total of 15 explants were set up in each culture flask. At various times following the establishment of the explants they were examined under a high power microscope to count the number of explants that had visible cell outgrowth onto the culture dish. Explants were counted as positive if at least one cell migrated from the explant tissue out onto the culture dish surface. Explants were followed for at least seven days. In experiment #1, the explants were cultured in the DMEM culture media supplemented with insulin and transferrin containing the following test samples: 1) Anti-PDGF alpha receptor MAb (169.31) at 50 µg/ml; 2) Anti-PDGF beta receptor MAb (163.31) at 50 µg/ml; or 3) DMEM media alone (control). In experiment #2 the explants were cultured in DMEM plus insulin and transferrin, and either 1) a pool of anti-PDGF alpha and beta receptor MAbs (169.31 and 163.31) at 25 µg/ml each; or 2) DMEM alone (control)

The results, presented as the mean percentage of explants positive for cell outgrowth ± SEM for each test condition (Table 5), demonstrate that the anti-PDGF receptor monoclonal antibodies, individually as well as in pools, are able to decrease the level of smooth muscle cell outgrowth from the baboon aortic explants when measured at either four or seven days. These finding indicate that these antibodies are able to inhibit processes required for cell migration through a solid matrix, such as could be required for cells to migrate through existing vascular tissue toward sites of intimal hyperplasia.

TABLE 5

Migration of Vascular Smooth Muscle Cells Out of Baboon Aortic Tissue Explants

| Sample | (n) | Day 4 | Day 7 |
|---|---|---|---|
| Experiment #1 | | | |
| Control | 7 | 11 +/– 4 | 61 +/– 4 |
| MAb 169.31 | 7 | 6 +/– 2 | 43 +/– 5 |
| MAb 163.31 | 7 | 6 +/– 5 | 38 +/– 5 |
| Experiment #2 | | | |
| Control | 11 | 9 +/– 3 | 58 +/– 4 |
| Pool | 11 | 2 +/– 1 | 36 +/– 6 |

(n): number of times experiment performed.

Example 12

Inhibition of PDGF Mitogenic Activity on Human Dermal Fibroblasts by Delayed Addition of Anti-PDGF Receptor Monoclonal Antibodies Human dermal fibroblasts were plated at approximately 20,000 cells per well in 24-well culture dishes and grown until quiescent in DMEM containing 2% fetal calf serum. The cells were stimulated with either PDGF-AA, AB or BB. Increasing concentrations of each of the PDGF ligands were added to the cells to generate standard curves of mitogenic potency for the three PDGF isoforms. The final PDGF concentrations used for the standards were 5, 2.5, 1.25, 0.62, 0.31, 0.15 and 0.0 ng/ml. 50× stock solutions of PDGF were made in 10 mM acetic acid containing 0.25% rabbit serum albumin. 25 µl of each of the stock solutions were added to triplicate test wells. To look for inhibitory activity by MAbs 162.62 and 169.14, wells containing the fibroblasts were incubated with 5 ng/ml of PDGF, final concentration. At various time intervals following the addition of the PDGF samples (1, 2, 4, 6 and 8 hours), a pooled sample of MAb 162.62 and MAb 169.14, 25 μg/ml final concentration for each MAb, was added to triplicate wells of the cells that had been treated with 5 ng/ml of PDGF. Nine hours after the addition of the PDGF samples, 50 μl of [$^3$H]thymidine, 20 μCi/ml in DMEM containing 1% fetal calf serum, was added to each well. The samples were incubated for an additional 13–15 hours at 37° C. The cells were washed with PBS, then harvested with trypsin and counted in a Betaplate™ liquid scintillation counter (Wallac).

The results, presented in Table 6, are given as mean cpm of [$^3$H]thymidine incorporated ± standard deviation, for triplicate determinations. The data are given for both the PDGF standard curves, and for the time course of antibody addition. The results demonstrate that there was a 75% decrease in the mitogenic activity for PDGF-AA when the anti-PDGF receptor antibodies were added to the cells as late as 8 hours following the addition of PDGF ligand. For both PDGF-AB and BB, the addition of the anti-PDGF receptor antibodies 8 hours after the addition of PDGF ligand caused a greater than 90% decrease in PDGF mitogenic activity. These studies demonstrated that the anti-PDGF receptor monoclonal antibodies can be added to cells at prolonged times after the presence of PDGF ligand and still have potent neutralizing effects against PDGF mitogenic activity.

TABLE 6

| PDGF-AA (ng/ml) | | | MAbs 162.62/169.14 | | |
|---|---|---|---|---|---|
| | cpm | | (PDGF-AA, 5 ng/ml) | | |
| ng/ml | +/− | (st. dev.) | Time in Hrs | cpm +/− | (st. dev.) |
| 5.0 | 7888 | (768) | 1 | 5400 | (870) |
| 2.5 | 7892 | (460) | 2 | 4350 | (431) |
| 1.25 | 6044 | (1126) | 4 | 5323 | (574) |
| 0.62 | 5569 | (315) | 6 | 5300 | (768) |
| 0.31 | 5072 | (224) | 8 | 6028 | (276) |
| 0.15 | 4888 | (393) | | | |
| 0.0 | 4804 | (320) | | | |
| PDGF-AB (ng/ml) | | | MAbs 162.62/169.14 | | |
| | cpm | | (PDGF-AA, 5 ng/ml) | | |
| ng/ml | +/− | (st. dev.) | Time in Hrs | cpm +/− | (st. dev.) |
| 5.0 | 16370 | (409) | 1 | 4372 | (443) |
| 2.5 | 16621 | (878) | 2 | 4783 | (401) |
| 1.25 | 14061 | (1066) | 4 | 4363 | (427) |
| 0.62 | 11238 | (238) | 6 | 5238 | (611) |
| 0.31 | 9206 | (428) | 8 | 5659 | (667) |
| 0.15 | 8061 | (1054) | | | |
| 0.00 | 5253 | (443) | | | |
| PDGF-BB (ng/ml) | | | MAbs 162.62/169.14 | | |
| | cpm | | (PDGF-AA, 5 ng/ml) | | |
| ng/ml | +/− | (st. dev.) | Time in Hrs | cpm +/− | (st. dev.) |
| 5.0 | 12427 | (1366) | 1 | 2811 | (291) |
| 2.5 | 15445 | (977) | 2 | 3076 | (169) |
| 1.25 | 13712 | (976) | 4 | 4298 | (574) |
| 0.62 | 11989 | (1248) | 6 | 5089 | (420) |
| 0.31 | 9482 | (2089) | 8 | 7335 | (502) |
| 0.15 | 6905 | (456) | | | |
| 0.00 | 3090 | (272) | | | |

Example 13

Displacement of Receptor-bound $^{125}$I-PDGF from Human Osteosarcoma Cells by Anti-PDGF Receptor MAbs The four MAbs 162.62, 163.31, 169.14 and 169.31 were analyzed for the ability to displace $^{125}$I-PDGF-AA and $^{125}$I-PDGF-BB bound to PDGF receptors on monolayers of human osteosarcoma cells (ATCC CRL 1427), which express approximately equal amounts of PDGFr-alpha and PDGFr-beta. Monolayers of human osteosarcoma cells, grown in 24-well culture plates, were incubated for 1 hour at 4° C. with $^{125}$I-PDGF-AA or $^{125}$I-PDGF-BB diluted in binding media. The cells were washed with PBS, then 1 ml of either binding media alone, MAb 169.14, 169.31, 162.62, 163.31, or a pool of 169.31 and 162.62 was added to each well. The antibodies were diluted in binding media and added to the cells at a concentration of 5 μg/ml, 1 ml/well. The cells were washed for 1 hour at 4° C., then with PBS, incubated with extraction buffer, then harvested and counted in a gamma counter to monitor the level of $^{125}$I-PDGF binding. 100 ng/ml of PDGF-BB was added to triplicate wells with $^{125}$I-PDGF-AA and $^{125}$I-PDGF-BB to determine the levels of non-specific binding. The results, presented in Table 7, are shown as specific cpm bound (std. dev.) for $^{125}$I-PDGF-AA and $^{125}$I-PDGF-BB following the second incubation with the test compounds listed. The % displacement value was determined by comparing the cpm bound for the test samples compared to the cpm bound in the binding medium alone wells. The results demonstrate that the anti-PDGF alpha receptor MAbs, 169.14 and 169.31, were able to displace approximately 63% of the prebound $^{125}$I-PDGF-AA. In contrast, the anti-PDGF beta receptor MAbs, 162.62 and 163.31, had essentially no effect, displacing less than 10% of the counts. For $^{125}$I-PDGF-BB binding, MAbs 169.14 and 169.31 were able to displace between 22–25% of the prebound counts while MAb 162.62 was able to displace 34% of the counts. The pool of 169.31 and 162.62 displaced of the prebound $^{125}$I-PDGF-BB. These results show that, in addition to being able to block PDGF binding, the anti-PDGF receptor MAbs are also able to displace prebound PDGF-AA and BB from cell-surface receptors.

TABLE 7

Ability of Anti-PDGF Receptor MAbs to Displace Recptor-bound $^{125}$I-PDGF-AA and $^{125}$I-PDGF-BB from Human Osteosarcoma Cells

| First Inc. | Second Inc. | CPM Bound | % Displacement |
|---|---|---|---|
| $^{125}$I-PDGF-AA | Binding Media | 458 (46) | 0 |
| " | 169.14 | 164 (91) | 64 |
| " | 169.31 | 174 (58) | 62 |
| " | 162.62 | 415 (18) | 9 |
| " | 163.31 | 420 (40) | 8 |
| " | 169.31/162.62 | 116 (24) | 75 |
| $^{125}$I-PDGF-BB | Binding Media | 528 (41) | 0 |
| " | 169.14 | 411 (87) | 22 |
| " | 169.31 | 395 (30) | 25 |
| " | 162.62 | 349 (48) | 34 |
| " | 163.31 | 518 (129) | 2 |
| " | 169.31/162.62 | 289 (58) | 44 |

Example 14

Inhibition of Baboon Serum and PDGF-BB Stimulated Smooth Muscle Cell Mitogenesis By Anti-PDGFr MAbs Applied Independently or Coordinately With Heparin Anti-PDGFr-alpha MAb 169.31 and anti-PDGFr-beta MAb 163.31 were analyzed independently, and in coordinate administration assays with heparin, to determine the ability of the antibodies to inhibit PDGF-BB and baboon serum mitogenic activity on BVSMCs.

To assess the activity of the two antibodies alone, and to assess combinatorial inhibitory activities of the antibodies coordinately administered with heparin, baboon venous smooth muscle cells, at passage 7 following outgrowth, were plated into 24-well tissue culture dishes at $3.0\times10^4$ cells per well in DMEM (GIBCO BRL) supplemented with 10% fetal bovine serum. The cells were maintained in this medium for three days at 37° C. in a 5% $CO_2$ atmosphere. The medium was then replaced with 1 ml/well of Mito Media, and the cells were cultured for an additional 24 hours.

In a first set of experiments, PDGF-BB was diluted with 10 mM acetic acid containing 0.25% rabbit serum albumin to a concentration of 40 ng/ml. 50 μl of this stock dilution was then added to each well to give a final concentration of 2 ng/ml on the cells. To certain of the test wells, unfractionated heparin (UH) (Sigma Chemical Co., St. Louis, Mo.) was added alone or coordinately administered with one or more of the anti-PDGFr antibodies. The UH employed for these studies was a mixture of heparin species of multiple sizes, with a specific activity of appproximately 150 Units/mg in a standard Activated Partial Thromboplastin Time (APTT) assay. The addition of heparin to the cells was done by diluting the heparin to a stock concentration of 400 μg/ml in PBS, and adding 25 μl of the heparin solution to the appropriate wells to give a final heparin concentration of 10 μg/ml on the cells. The anti-PDGFr antibodies were diluted with PBS to give 40× stock concentrates, then 25 μl of the antibody dilution was added to appropriate test wells. Those wells receiving only antibody or heparin independently received 25 μl of PBS as a buffer control.

A dose-response profile for PDGF-BB stimulation was generated by making 2-fold dilutions of the PDGF with 10 mM acetic acid containing rabbit serum albumin and adding 50 μl of the stock solutions to appropriate wells to give final PDGF-BB concentrations on the cells of 2, 1 and 0.5 ng/ml.

After addition of the treatments, the cells were incubated for 20 hours at 37° C. Mitogenic stimulation of BVSMCs was assessed by measuring the uptake of [$^3$H]thymidine. 50 μl of a 20 μCi/ml [$^3$H]thymidine stock solution, made up in DMEM, was added directly to the cells for a final concentration of 1 μCi/well. The cells were incubated for 4 hours at 37° C., washed once with PBS, treated with 0.25 ml of trypsin until cells detached, and harvested onto a filter using a cell harvester (LKB Wallac). The filters were counted using a Betaplate™ liquid scintillation counter (Wallac).

The data for antibody and antibody/heparin inhibition of PDGF-BB stimulation are shown in Table 8. Data in Table 8 are presented as mean counts per minute (cpm) of [$^3$H] thymidine incorporated by baboon smooth muscle cells stimulated with PDGF-BB. Values of percent inhibition were determined directly from the measured decrease in incorporation of [$^3$H]thymidine. A dose-response table of PDGF-BB mitogenic activity is included in Table 8. In Experiment #1, the addition of antibody 169.31 to cells stimulated with PDGF-BB caused a marked inhibition in [$^3$H]thymidine incorporation at antibody doses of 1 and 0.1 μg/ml. The administration of heparin to the cells coordinately with antibody 169.31 resulted in a combinatorially effective antimitogenic result, i.e. [$^3$H]thymidine incorporation was inhibited to a greater extent than was measured for either the antibody or heparin administered alone. Analysis of antibody 163.31, Experiment #1, showed that a dose of 25 μg/ml was also able to inhibit [$^3$H]thymidine incorporation, but at a much lower level than observed for antibody 169.31. When heparin was added along with antibody 163.31, a combinatorially effective inhibition was also observed, but this effect was only seen at higher antibody concentrations. The coordinate application of antibodies 169.31 (1 μg/ml) and 163.31 (25 μg/ml) also resulted in a combinatorially antimitotic result, wherein inhibition of PDGF-BB-stimulated [$^3$H]thymidine incorporation by the BVSMCs was greater than that observed following administration of either antibody alone.

In Experiment #2, antibodies 169.31 and 163.31 were further analyzed, both independently and in coordinate administration assays with one another or with heparin (UH, 10 μg/ml), to determine the anti-mitotic activities of these various treatments on PDGF-BB-stimulated [$^3$H]thymidine incorporation by BVSMCs. Similar to the results of Experiment #1, the coordinate administration of the two antibodies provided more effective inhibition of mitogenic activity on BVSMCs than administration of either antibody alone. In addition, coordinate administration of heparin with a pool of the two antibodies led to combinatorially effective inhibition above inhibitory activity provided by the heparin or antibody pool alone.

In sum, these data demonstrate that the coordinate administration of heparin with either of the anti-PDGFr-alpha or anti-PDGFr-beta antibodies or with a pool of the two antibodies, as well as the coordinate administration of the antibodies with one another, can provide a combinatorially effective treatment against PDGF-BB mitogenic activity on BVSMCs.

TABLE 8

Inhibition of PDGF-BB Mitogenic Activity By Anti-PDGFr MAbs Administered Independently or Coordinately With Heparin

EXPERIMENT 1

[$^3$H]Thymidine Incorporation

| MAb (μg/ml) | | | | | |
|---|---|---|---|---|---|
| 163.31 | 169.31 | (−) Heparin | % Inhib. | (+) Heparin | % Inhib. |
| 0 | 0 | 4,714 | 0% | 2,543 | 46% |
| 0 | 1 | 2,271 | 52% | | |
| 0 | 0.1 | 2,637 | 44% | 1,582 | 66% |
| 0 | 0.01 | 4,078 | 13% | 1,983 | 58% |
| 0 | 0.001 | 4,486 | 05% | 2,311 | 51% |
| 25 | 0 | 3,969 | 16% | 1,844 | 61% |
| 5 | 0 | 4,460 | 05% | 2,484 | 47% |
| 1 | 0 | 4,268 | 09% | 2,559 | 46% |
| 0.2 | 0 | 4,504 | 04% | 2,671 | 43% |
| 25 | 1 | 1,015 | 78% | | |
| 5 | 1 | 1,859 | 61% | | |
| 1 | 1 | 2,007 | 57% | | |
| 1 | 0.2 | 1,979 | 58% | | |
| 1 | 0.04 | 2,090 | 56% | | |
| 0 | 0 | 4,414 | 06% | | |

PDGF-BB Dose-Response

| PDGF-BB (ng/ml) | CPM |
|---|---|
| 2.0 | 4,714 |
| 1.0 | 2,313 |
| 0.5 | 1,588 |
| 0.0 | 161 |

TABLE 8-continued

Inhibition of PDGF-BB Mitogenic Activity By Anti-PDGFr MAbs Administered Independently or Coordinately With Heparin

EXPERIMENT 2

| MAb (µg/ml) | | [³H]Thymidine Incorporation | | | |
|---|---|---|---|---|---|
| 163.31 | 169.31 | (−) Heparin | % Inhib. | (+) Heparin | % Inhib. |
| 0 | 0 | 3,469 | 0% | 2,116 | 39% |
| 0 | 1 | 2,283 | 34% | | |
| 0 | 0.1 | 2,183 | 37% | | |
| 0 | 0.01 | 2,778 | 20% | | |
| 25 | 0 | 2,139 | 38% | | |
| 5 | 0 | 3,425 | 01% | | |
| 1 | 0 | 3,958 | 0% | | |
| 25 | 1 | 797 | 77% | 540 | 85% |
| 5 | 1 | 1,595 | 54% | 999 | 71% |
| 1 | 1 | 1,976 | 43% | 1,201 | 65% |
| 0 | 1 | 2,283 | 34% | 1,551 | 55% |

Inhibition of the mitogenic activity of baboon serum was tested in a parallel set of experiments. The experiments were performed essentially as described above, with baboon serum added to the test wells at a final concentration of 1.25% by diluting the serum 1:4 with PBS and adding 50 µl of the diluted serum to each well. A dose-response profile for baboon serum stimulation was generated by making 2-fold dilutions of the baboon serum in PBS and adding 50 µl of the appropriate dilutions to give final serum concentrations on the cells of 1.25, 0.62, 0.31 and 0.15%.

The data for antibody and antibody/heparin inhibition of serum mitogenic activity on BVSMCs are presented in Table 9. These data show that monoclonal antibody 169.31 had minimal inhibitory effect on [³H]thymidine incorporation stimulated by the addition of 1.25% baboon serum, at doses of antibody up to 1 µg/ml. When heparin was coordinately administered to the cells along with antibody 169.31, the level of inhibition observed was no greater than the inhibitory activity exhibited by heparin alone. In contrast, the assays involving monoclonal antibody 163.31 showed significant inhibition of [³H]thymidine incorporation at an antibody concentration of 25 µg/ml. Moreover, when heparin was administered coordinately with antibody 163.31, there was a marked combinatorially effective inhibition of mitogenic activity as measured by [³H]thymidine incorporation, i.e. well above the antimitogenic effects observed for either the antibody or heparin alone. This combinatorially effective inhibition was particularly pronounced at MAb 163.31 concentrations between 0.2 µg/ml and 5 µg/ml.

Coordinate administration of 1 µg/ml of antibody 169.31 with increasing doses of antibody 163.31 showed a dose-dependent inhibition of [³H]thymidine incorporation. The coordinate administration of antibody 169.31 with antibody 163.31 also resulted in a pronounced combinatorially effective inhibition of serum mitogenic activity as shown in Table 9.

Data in Table 9 are presented as mean counts per minute (cpm) of [³H]thymidine incorporated by baboon smooth muscle cells stimulated with 1.25% baboon serum. Values of percent inhibition were calculated from a standard curve generated using the serum dose-response data presented.

TABLE 9

Inhibition of Baboon Serum Stimulated Smooth Muscle Cell Mitogenesis By Anti-PDGFR MAbs Administered Independently or Coordinately With Heparin

| MAb (µg/ml) | | [³H]Thymidine Incorporation | | | |
|---|---|---|---|---|---|
| 163.31 | 169.31 | (−) Heparin | % Inhib. | (+) Heparin | % Inhib. |
| 0 | 0 | 1,297 | 0% | 957 | 31% |
| 0 | 1 | 1,028 | 24% | | |
| 0 | 0.1 | 1,242 | 4% | 924 | 33% |
| 0 | 0.01 | 1,114 | 16% | 855 | 38% |
| 0 | 0.001 | 1,482 | 0% | 922 | 33% |
| 25 | 0 | 591 | 57% | 451 | 73% |
| 5 | 0 | 924 | 33% | 474 | 70% |
| 1 | 0 | 895 | 35% | 587 | 59% |
| 0.2 | 0 | 980 | 28% | 651 | 50% |
| 25 | 1 | 362 | 82% | | |
| 5 | 1 | 481 | 70% | | |
| 1 | 1 | 598 | 56% | | |
| 1 | 0.2 | 761 | 44% | | |
| 1 | 0.04 | 893 | 35% | | |

Serum Dose-Response

| (% NBS) | (CPM) |
|---|---|
| 1.25 | 1,297 |
| 0.62 | 639 |
| 0.31 | 410 |
| 0.15 | 317 |
| 0 | 161 |

Example 15

Inhibition of Serum Mitogenic Activity on Baboon Vascular Smooth Muscle Cells By Heparin Administered Alone, or Coordinately Administered With Anti-PDGFr MAbs Both unfractionated heparin (UH) (Sigma, St. Louis, Mo.) and low molecular weight heparin (LMWH) (Logiparin®, Novo Nordisk, Bagsvaerd, Denmark) were evaluated for their ability to inhibit the mitogenic activity of baoon serum on baboon vascular smooth muscle cells. Each form of heparin was administered to the cells independently or coordinately with anti-PDGFr MAbs. The LMWH used for these studies was generated by heparinase treatment of an unfractionated heparin, and is composed of heparin species with an average molecular weight of 5,500 daltons. The LMWH has a decreased antithrombotic activity compared to unfractionated heparin in an APTT assay, estimated at about 50 Units/mg.

To assess the anti-mitogenic activity of the two heparin preparations, with and without coordinately administered anti-PDGFr antibodies, BVSMCs from aortic explants (designated BO54 cells) were plated into 24-well tissue culture dishes at 2.5×10⁴ cells per well in DMEM (GIBCO BRL) supplemented with 10% fetal bovine serum. The cells were maintained in this media for three days at 37° C. in a 5% $CO_2$ atmosphere. The media was then replaced with 1 ml/well of Mito Media, and the cells were cultured in this media for an additional 24 hours.

Baboon serum was added to the test wells at a final concentration of 2.5%. This was done by diluting the serum 1:1 with PBS and adding 50 µl of the diluted serum to each well. To analyze heparin preparations for their inhibition of baboon serum-stimulated DNA synthesis in baboon smooth muscle cells, the heparin was added to the cells either independently or coordinately with the two anti-PDGFr monoclonal antibodies. The heparin samples were diluted with PBS to give a 400 µg/ml concentrate, then 25 µl of the concentrate was added to each test well to give a final heparin concentration of 10 µg/ml. Control wells received phosphate buffered saline only. Anti-PDGFr-alpha MAb 169.31 and anti-PDGFr-beta MAb 163.31 were diluted with PBS to 40 µg/ml and 1 mg/ml, respectively, and 25 µl of the diluted antibodies was added to appropriate test wells to give final antibody concentrations of 1 µg/ml for MAb 169.31 and 25 µg/ml for MAb 163.31.

After the addition of the treatments, the cells were incubated for 20 hours at 37° C. Mitogenic stimulation of the smooth muscles cells was assessed by measuring cellular incorporation of [$^3$H]thymidine as disclosed in Example 14.

The results of this study are presented in Table 10. Those cells treated with serum only in the absence of either heparin or anti-PDGFr MAbs had a control value for [$^3$H]thymidine incorporation of 36,032 cpm/well. Treatment of the cells with coordinately administered anti-PDGFr-alpha and anti-PDGFr-beta monoclonal antibodies caused a decrease in [$^3$H]thymidine incorporation to 27,000 cpm (i.e. a 25% inhibition of serum-stimulated DNA synthesis). There was no significant reduction in [$^3$H]thymidine incorporation when the cells were treated with either UH or LMWH alone. However, a significant decrease in [$^3$H]thymidine incorporation was observed when either the UH or the LMWH was added to the cells coordinately with the pool of anti-PDGFr antibodies. The data demonstrate that both UH and LMWH, when coordinately administered with a pool of anti-PDGFr-alpha and anti-PDGFr-beta antibodies, inhibit the mitogenic activity of autologous serum on BVSMCs in a combinatorially effective manner. Here again, the degree of combinatorially effective inhibition achieved demonstrates a synergistic or potentiating relationship between the antibody and heparin in the particular coordinate administration regime tested.

TABLE 10

| Antibody Treatment | (−) Heparin | (+) UH | (+) LMWH |
|---|---|---|---|
| Control | 36,032 +/− 4,512 | 34,912 +/− 5,617 | 34,140 +/− 2,667 |
| (% Inhibition) | | (3%) | (5%) |
| Anti-PDGFR | 27,005 +/− 2,227 | 12,377 +/− 3,785 | 19,967 +/− 974 |
| (% Inhibition) | (25%) | (66%) | (45%) |

Data are presented as mean +/− standard deviation for counts per minute (CPM) of [$^3$H]thymidine incorporated by baboon smooth muscle cells stimulated with 2.5% baboon serum. Percent inhibition of cpm incorporated from control value, in the absence of both added heparin and anti-PDGFR antibody, is presented in parentheses. Values of percent inhibition were determined directly from the measured decrease in incorporation of [$^3$H]thymidine, rather than by comparison to a dose-response curve for serum stimulation.

Example 16

Dose-Response of Inhibition of Serum Mitogenic Activity On Baboon Vascular Smooth Muscle Cells By Anti-PDGFr MAbs Coordinately Applied With Unfractionated Heparin or Low Molecular Weight Heparin A dose-response assay of anti-PDGFr beta monoclonal antibody 163.31, in the presence of a constant amount of anti-PDGFr alpha antibody 169.31 (1 µg/ml), was performed to evaluate concentration dependence of anti-PDGFr MAb inhibition of DNA synthesis in BVSMCs stimulated by baboon serum. This dose-response was evaluated in the absence of any added heparin, as well as in the presence of 10 µg/ml of either an unfractionated heparin (UH) with an antithrombtic activity of about 150 Units/mg by APPT assay (Sigma Chemical Co., St. Louis, Mo.) or a low molecular weight heparin (LMWH) (Logiparin®, approximately 50 Units/mg by APPT assay) (Novo Nordisk, Bagsvaerd, Denmark).

For these dose-response studies, BVSMCs from aortic explants (BO54 cells) were plated into 24-well tissue culture dishes at 2.5×10$^4$ cells per well in DMEM supplemented with 10% fetal bovine serum. After 3 days the media was changed to Mito Media, and the cells were cultured for an additional 24 hours. The cells were stimulated to undergo mitosis by the addition of 50 µl/well of baboon serum that had been diluted 1:1 with PBS, giving a final serum concentration of 2.5% on the cells. MAb 163.31 was diluted with PBS to make 40× concentrates, and 25 µl of the diluted antibody was added to the test wells to give final antibody concentrations on the cells ranging from 25 µg/ml to 1.25 µg/ml. 25 µl of a 40 µg/ml solution of MAb 169.31 was simultaneously added to the wells to give a final antibody concentration of 1 µg/ml in all of the 163.31 treated wells. The combination of monoclonal antibodies 163.31 and 169.31 was tested in the absence of any added heparin and, alternatively, in a coordinate administration assay with either UH or LMWH. The two heparin preparations were diluted with PBS to a final concentration of 400 µg/ml, and 25 µl of concentrate was added to appropriate wells to give a final heparin concentration on the cells of 10 µg/ml. PBS only was added to those test wells not receiving heparin.

After the addition of the treatments, the cells were incubated for 20 hours at 37° C. Mitogenic activity was assessed by measuring the uptake of [$^3$H]thymidine as disclosed in Example 14.

The results of this study are presented in Table 11. In the absence of heparin, a significant decrease in mitotic activity of the BVSMCs was observed only in those wells receiving the 25 and 10 µg/ml doses of monoclonal antibody 163.31. However, in the presence of either UH or LMWH, all concentrations of monoclonal antibody 163.31 tested (in the presence of a constant amount of MAb 169.31) provided significant combinatorially effective inhibition, with essentially identical results obtained for the two heparin preparations. In the presence of heparin, the 1.25 µg/ml dose of 163.31 was more effective at inhibiting DNA synthesis than the 25 µg/ml dose of 163.31 in the absence of heparin. The presence of either UH or LMWH administered independent of any antibody had only a minimal effect on the mitogenic activity of serum.

TABLE 11

| MAb (µg/ml) | | CPM ± Std. Dev. (% Inhibition) | | |
|---|---|---|---|---|
| 163.31 | 169.31 | (−) Heparin | (+) UH | (+) LMWH |
| 0 | 0 | 31,002 ± 2,655 | 27,175 ± 1,518 (12%) | 27,573 ± 947 (11%) |
| 25 | 1 | 23,424 ± 371 (24%) | 11,811 ± 365 (62%) | 13,095 ± 409 (58%) |
| 10 | 1 | 23,901 ± 4,138 (23%) | 12,317 ± 2,034 (60%) | 11,829 ± 1,451 (62%) |
| 5 | 1 | 29,366 ± | 18,449 ± 1,802 | 18,832 ± 1,530 |

TABLE 11-continued

| MAb (μg/ml) | | CPM ± Std. Dev. (% Inhibition) | | |
|---|---|---|---|---|
| 163.31 | 169.31 | (−) Heparin | (+) UH | (+) LMWH |
| | | 1,652 (5%) | (40%) | (39%) |
| 2.5 | 1 | 27,192 ± 2,351 (12%) | 16,249 ± 4,075 (48%) | 16,720 ± 2,674 (46%) |
| 1.25 | 1 | 29,032 ± 1,012 (6%) | 19,663 ± 1,455 (37%) | 21,664 ± 1,485 (31%) |

Data are presented as mean ± standard deviation for counts per minute (CPM) of [$^3$H]thymidine incorporated by baboon smooth muscle cells stimulated with 2.5% baboon serum. UH = Unfractionated heparin, LMWH = Low molecular weight heparin. Values of percent inhibition were determined directly from the measured decrease in incorporation of [$^3$H]thymidine.

Example 17

Comparison of Antimitogenic Activities of Murine Anti-PDGFr-Alpha MAb 169.31 With Mouse/Human Chimeric Anti-PDGFr-Alpha Antibody A mouse/human chimeric antibody was generated using the anti-PDGFr-alpha monoclonal antibody 169.31 as the parent antibody for cloning out the light and heavy-chain variable domains. This mouse/human chimeric antibody comprises the variable domains of the parent murine monoclonal antibody and the constant domains for human IgG4 heavy-chain and human kappa light-chain. Construction of this antibody used standard techniques as described in Mountain and Adair, Biotech. and Genet. Eng. Rev. 10: 1–142, 1992; and Adair et al, Immunol. Rev. 130: 5–40, 1992. The parent murine antibody and the mouse/human chimeric antibody were directly compared for their ability to inhibit DNA synthesis of BVSMCs (BO54) stimulated with 2% baboon serum.

The parent murine and the chimeric anti-PDGFr-alpha antibodies were analyzed at both 1.0 and 0.1 μg/ml in the presence of 10 μg/ml of murine anti-PDGFr-beta antibody 163.31 and 10 μg/ml of an unfractionated heparin (Elkins-Sinn, Inc., Cherry Hill, N.J.; specific activity ≅150 units/mg). In addition, both anti-PDGFr-alpha antibodies (1 μg/ml) were added to the cells in the presence of 10 μg/ml of chimeric anti-PDGFr-beta antibody (see Example 18) and 10 μg/ml of heparin. The results, presented in Table 12, demonstrate that both the parent murine MAb 169.31 and the mouse/human chimeric anti-PDGFr-alpha antibody have similar inhibitory potency in the presence of either the parent murine anti-PDGFr-beta MAb 163.31 or the mouse/human chimeric anti-PDGFr-beta antibody.

TABLE 12

Antimitogenic Activities of Parent Murine and Mouse/Human Chimeric Anti-PDGFr-Alpha Antibodies Coordinately Administered With Heparin

| Serum (2%) | Anti-PDGFr alpha (μg/ml) | | Anti-PDGFr beta (10 μg/ml) | Heparin | CPM ± S.D. |
|---|---|---|---|---|---|
| + | Buffer | | Buffer | No | 7,242 ± 329 |
| − | Buffer | | Buffer | No | 71 ± 6 |
| + | 169.31 | (1.0) | 163.31 | Yes | 2,278 ± 321 |
| + | 169.31 | (0.1) | 163.31 | Yes | 3,225 ± 366 |
| + | Ch 169 | (1.0) | 163.31 | Yes | 2,879 ± 620 |
| + | Ch 169 | (0.1) | 163.31 | Yes | 3,279 ± 985 |
| + | 169.31 | (1.0) | Ch 163 | Yes | 2,715 ± 170 |
| + | Ch 169 | (1.0) | Ch 163 | Yes | 2,600 ± 575 |

Data are presented as counts per minute (cpm) ± standard deviation of [$^3$H]thymidine incorporated by baboon SMCs following stimulation with 2% baboon serum. Ch 169 = Mouse/human chimeric anti-PDGFr-alpha antibody, Ch 163 = Mouse/human chimeric anti-PDGFr-beta antibody.

Example 18

Comparison of Antimitogenic Activities of Murine Anti-PDGFr-Beta MAb 163.31 With Mouse/Human Chimeric Anti-PDGFr-Beta Antibody A mouse/human chimeric anti-PDGFr-beta antibody was generated using the murine anti-PDGFr-beta monoclonal antibody 163.31 as the parent antibody for cloning out the light and heavy-chain variable domains. This mouse/human chimeric antibody comprises the variable domains of the parent murine monoclonal antibody and the constant domains for human IgG4 heavy-chain and human kappa light-chain. Construction of this antibody used the same standard techniques for chimeric antibody construction as described above for the chimeric anti-PDGFr-alpha antibody (Example 17). The parent murine antibody and the mouse/human chimeric antibody were directly compared for their ability to inhibit DNA synthesis in baboon smooth muscle cells stimulated with 2.0% baboon serum.

BVSMCs (BO54) were plated at a density of 2×10$^4$ cells/well in 24-well culture plates and grown for approximately 48 hours in DMEM containing 10% fetal calf serum at 37° C. The cells were then incubated for 24 hours in Mito Media to allow them to become quiescent.

A control plate of cells was stimulated with a two-fold dilution series of normal baboon serum (2.0% to 0.125%) to produce a standard curve. The serum was diluted in PBS, and 50 μl of a 20× stock was added directly to the wells in triplicate.

A dilution series of the anti-PDGFr-beta MAb 163.31, or the chimeric anti-PDGFr-beta antibody, was administered coordinately in appropriate test wells with the anti-PDGFr-alpha MAb 169.31 (1 μg/ml) and unfractionated heparin (2 Units/ml) (Elkins-Sinn, Inc., Cherry Hill, N.J.) to assess inhibitory effects of these treatments on BVSMCs stimulated by 2.0% baboon serum. In addition, the anti-PDGFr-beta parent and chimeric antibodies were analyzed in independent administration assays and in coordinate administration assays using the antibody and heparin. The antibodies and heparin were added to appropriate test wells at 25 μl per well of a 40× stock diluted in PBS. The antibody concentrations used are indicated in Table 13.

After administration of the test samples, the cells were incubated for 18 hours at 37° C. Mitogenic activity was assessed by uptake of [$^3$H] thymidine.

The results of the anti-PDGFr-beta MAb dose-response experiment, presented in Table 13, demonstrate that baboon serum-induced mitogenic activity was inhibited approximately 80% by a combination of 25 µg/ml 163.31, 1 µg/ml 169.31 and 2 Units/ml heparin. Similar results were obtained using the chimeric anti-PDGFr-beta MAb. Coordinate administration of each of the murine and chimeric anti-PDGFr-beta MAb, at 25 µg/ml, with the anti-PDGFr-alpha MAb 169.31, resulted in approximately 30% inhibition of baboon serum mitogenic activity. The anti-PDGFr-beta MAbs coordinately administered with heparin produced roughly 40% inhibition. Each of the antimitogenic agents, when administered independently, resulted in less than 30% inhibition of baboon serum mitogenic activity.

These results demonstrate that the mouse/human chimeric anti-PDGFr-beta antibody has similar inhibitory activity as that of the parent murine anti-PDGFr-beta antibody MAb 163.31. This activity provides a combinatorially effective inhibition of serum mitogenic activity on BVSMCs when the chimeric anti-PDGFr-beta antibody is administered coordinately with either the anti-PDGFr-alpha MAb 169.31, heparin, or a combination of anti-PDGFr-alpha MAb and heparin.

TABLE 13

Comparison of Antimitogenic Activities of Murine Anti-PDGFr-Beta MAb 163.31 and Mouse/Human Chimeric Anti-PDGFr-Beta in Independent and Coordinate Administration Assays With Anti-PDGFr-Alpha MAb and Heparin

| MAb (µg/ml) | | CPM ± S.D. (Percent Inhibition) | |
|---|---|---|---|
| 163.31 | 169.31 | (−) Heparin | (+) UH |
| 0 | 0 | 7539 ± 554 (0%) | 5,975 ± 383 (27%) |
| 25 | 0 | 6,580 ± 449 (18%) | 4,786 ± 423 (41%) |
| 0 | 1 | 8,802 ± 641 (0%) | 6,479 ± 1,120 (20%) |
| 1.56 | 1 | — | 3,973 ± 588 (52%) |
| 6.25 | 1 | — | 2,861 ± 177 (66%) |
| 25 | 1 | 5,791 ± 957 (29%) | 1,495 ± 16 (83%) |

| Antibody (µg/ml) | | CPM ± S.D. (Percent Inhibition) | |
|---|---|---|---|
| Chimeric 163 | Mab 169.31 | (−) Heparin | (+) UH |
| 0 | 0 | 7539 ± 554 (0%) | 5,975 ± 383 (27%) |
| 25 | 0 | 6,721 ± 0 (16%) | 4,878 ± 427 (40%) |
| 0 | 1 | 8,802 ± 641 (0%) | 6,479 ± 1,120 (20%) |
| 1.56 | 1 | — | 4,528 ± 899 (45%) |
| 6.25 | 1 | — | 2,892 ± 382 (65%) |
| 25 | 1 | 5,164 ± 519 (37%) | 1,973 ± 374 (77%) |

Data are presented as the counts per minute (cpm)±standard deviation of [$^3$H]thymidine incorporated by baboon SMCs following stimulation with 2% baboon serum. Values of percent inhibition for both the parent and chimeric antibody studies were determined by comparing the cpm incorporated of [$^3$H]thymidine to a standard curve generated from the serum dose-response data presented below.

| Serum Dose-Response | |
|---|---|
| (% NBS) | (CPM ± S.D.) |
| 0 | 89 ± 0 |
| 0.125 | 444 ± 89 |
| 0.25 | 978 ± 62 |
| 0.5 | 2,190 ± 46 |
| 1 | 4,655 ± 248 |
| 2 | 7,768 ± 585 |

Example 19

Dose-Responsive Inhibition of Serum Mitoqenic Activity on Baboon Vascular Smooth Muscle Cells by Heparin Administered Independently or Coordinately With Anti-PDGFr Antibodies Baboon smooth muscle cells (BO54) were plated at a density of $2 \times 10^4$ cells/well in 24-well culture plates and grown for approximately 72 hours in DMEM containing 10% fetal calf serum at 37° C. The cells were then made quiescent by incubating them for 24 hours in Mito Media. The ability of heparin alone to inhibit mitogenic stimulation by 2% baboon serum was tested by adding a dilution series of either an unfractionated heparin (UH; approximately 150 Units/mg) (Elkins-Sinn, Inc.) or low molecular weight heparin (LMWH; Logiparin®, approximately 50 Units/mg) (Novo Nordisk, Bagsvaerd, Denmark) to the cells at doses ranging from 15 U/ml to 0.06 U/ml (final concentation on the cells). The same dilution series for both types of heparin was also tested in the presence of anti-PDGFr-beta MAb 163.31 (10 µg/ml) and anti-PDGFr-alpha MAb 169.31 (1 µg/ml).

After the addition of the treatments the cells were incubated for 18 hours at 37° C. Serum mitogenic activity was assessed by measuring uptake of [$^3$H]thymidine. The results of the heparin dose-response experiments are presented in Table 14. Heparin alone at the highest doses tested had only a modest inhibitory effect on [$^3$H]thymidine incorporation by BVSMCs, while the same doses coordinately administered with the anti-PDGF receptor antibodies combinatorially inhibited up to 90% of the serum mitogenic activity. Assuming a specific activity of 150 U/mg for the Elkins-Sinn unfractionated heparin, and 50 U/mg for the low molecular weight heparin, the highest doses used for the two heparin preparations were about 100 and 300 µg/ml, respectively. At these concentrations in the independent administration assays there was only minimal inhibition of mitogenic activity. In contrast, at heparin doses 100-fold lower there was still a significant combinatorially effective increase in inhibitory activity when the heparin was coordinately administered with the anti-PDGFr antibodies. These results demonstrate that significantly lower doses of heparin can be used to act in a combinatorially effective fashion with the anti-PDGFr antibodies to inhibit [$^3$H] thymidine incorporation, well above levels of inhibition achieved with the antibodies or heparin alone.

TABLE 14

Dose-Responsive Inhibition of Serum Mitogenic Activity by Heparin Administered Independently or Coordinately With Anti-PDGFr Antibodies

| | | | (+) MAb 163.31 (10 μg/ml) (+) MAb 169.31 (1 μg/ml) | |
|---|---|---|---|---|
| UH (U/ml) | cpm | Std. Dev. | cpm | Std. Dev. |
| 0 | 4,694 | 586 | 3,532 | 276 |
| 0.06 | 5,816 | 495 | 2,662 | 377 |
| 0.18 | 4,653 | 368 | 2,030 | 246 |
| 0.55 | 4,900 | 527 | 1,133 | 157 |
| 1.67 | 4,473 | 405 | 714 | 56 |
| 5 | 4,451 | 357 | 526 | 43 |
| 15 | 3,628 | 255 | 369 | 16 |
| LMWH (U/ml) | cpm | Std. Dev. | cpm | Std. Dev. |
| 0 | 5,715 | 665 | 2,904 | 28 |
| 0.06 | 5,169 | 438 | 2,355 | 301 |
| 0.18 | 4,535 | 728 | 1,038 | 124 |
| 0.55 | 4,210 | 392 | 1,151 | 60 |
| 1.67 | 4,207 | 2422 | 641 | 9 |
| 5 | 3,642 | 734 | 678 | 52 |
| 15 | 3,457 | 369 | 380 | 35 |

Example 20

Inhibition of Smooth Muscle Cell Outmigration from Baboon Aortic Explants by Coordinate Administration of Anti-PDGFr MAbs and Heparin Anti-PDGFr monoclonal antibodies were further tested in the presence or absence of heparin for their ability to decrease rates of baboon vascular smooth muscle cell outmigration from explants of baboon aortic tissue. Baboon aortic explants were set up essentially as described in Example 11. The explants were cultured in DMEM supplemented with insulin and transferin and containing the following test samples: 1) Anti-PDGFr-alpha MAb (169.31) and anti-PDGFr-beta MAb (163.31), each antibody at 25 μg/ml, 2) Unfractionated heparin (Sigma Chemical Co.) (100 μg/ml), 3) Anti-PDGF alpha receptor MAb (169.31) and anti-PDGF beta receptor MAb (163.31) (25 μg/ml each) and unfractionated heparin (100 μg/ml), and 4) DMEM (control).

The results, presented in Table 15, demonstrate that, when measured at 7 days following establishment of the explants, heparin alone decreased the level of smooth muscle cell outmigration to 82% of control, while the anti-PDGF receptor antibody combination decreased the outgrowth to 64% of control. Coordinate administration of both the anti-PDGF receptor antibodies and heparin further decreased the level of outmigration to 42% of control. Thus, heparin and the anti-PDGF receptor antibodies combinatorially inhibited smooth muscle cell outmigration in the coordinate administration regimes tested.

TABLE 15

Inhibition of Smooth Muscle Cell Outgrowth from Baboon Aortic Tissue Explants by Combination of Anti-PDGFr MAbs and Heparin

| Condition | n | Mean | St. Dev. | % Control |
|---|---|---|---|---|
| Control | 7 | 65.6 | 16.8 | — |
| Anti-PDGFr | 7 | 41.9 | 22.1 | 63.8 |
| Heparin | 7 | 53.7 | 17.2 | 81.9 |

TABLE 15-continued

Inhibition of Smooth Muscle Cell Outgrowth from Baboon Aortic Tissue Explants by Combination of Anti-PDGFr MAbs and Heparin

| Condition | n | Mean | St. Dev. | % Control |
|---|---|---|---|---|
| Heparin + Anti-PDGFr | 7 | 27.7 | 13.5 | 42.3 |

Example 21

Saturation Binding Analysis of MAb 163.31 on B054 Cells in the Presence and Absence of Heparin The binding ability of anti-PDGFr-beta MAb 163.31 on baboon smooth muscle cells (BO54) was tested in the presence and absence of heparin. Baboon smooth muscle cells (BO54) were plated at a density of 20,000 cells/well in 24-well culture plates and grown for approximately 48 hours at 37° C. in DMEM containing 10% fetal calf serum. The cells were incubated for 24 hours in Mito Media to become quiescent, then washed once with 4° C. binding media (DMEM/Hams F-12, 25mM Hepes, 0.1%BSA). The binding activity of MAb 163.31 on PDGF-beta receptors was analyzed in the presence of heparin by adding four-fold dilutions of $^{125}$I-labeled MAb 163.31 ($^{125}$I-163.31) in 4° C. binding media (ranging from $2.1 \times 10^6$ to $1 \times 10^3$ cpm/ml) and 10 μg/ml heparin (Elkins-Sinn, Inc.) to the appropriate wells in triplicate in 1 ml aliquots. On a separate plate, the same dilution series of $^{125}$I-163.31 was added without heparin. To determine the level of nonspecific binding by a $^{125}$I-163.31, set of triplicate wells was set up on each plate containing $5.5 \times 10^5$ cpm/well of the $^{125}$I-163.31 plus 25 μg/ml unlabeled 163.31. The plates were kept on ice while samples were being added, then incubated for 1.5 hour at 4° C. on a rotary shaker. After washing 3× with PBS, the cells were incubated with an extraction buffer (PBS, 1% NP-40), and the extracts were harvested to 12×75 mm tubes and counted in a gamma counter. The results of the binding studies, presented in Table 16, demonstrate that the coordinate addition of heparin and antibody had no significant effect on antibody binding. Thus, the combinatorial effectiveness of coordinately administering heparin with the anti-PDGFr-beta antibodies, shown in the above examples, does not appear to be attributable to any stimulation by heparin of binding of the antibody to cell-surface PDGF-beta receptors.

TABLE 16

Saturation Binding Analysis of MAb 163.31 on Baboon Vascular Smooth Muscle Cells in the Presence and Absence of Heparin

| $^{125}$I-163.31 | Mean Specific cpm +/− Std. Dev. | |
|---|---|---|
| Applied cpm | (+) Heparin | (−) Heparin |
| 2,100,000 | 8,956.0 ± 678.1 | 9,235.0 ± 632.3 |
| 555,000 | 2,036.0 ± 62.8 | 2,301.0 ± 329.0 |
| 148,000 | 604.0 ± 56.5 | 685.0 ± 8.5 |
| 46,000 | 165.2 ± 12.3 | 212.0 ± 16.6 |
| 11,000 | 84.7 ± 9.0 | 81.0 ± 3.8 |

Example 22

Saturation Binding Analysis of PDGF-BB on Baboon Vascular Smooth Muscle Cells in the Presence and Absence of Heparin The ability of PDGF-BB to bind its receptor on baboon vascular smooth muscle cells was tested in the presence and absence of heparin. Baboon smooth muscle cells (BO54) were plated at a density of 20,000 cells/well in 24-well culture plates and grown for approximately 48 hours at 37° C. in DMEM containing 10% fetal calf serum. The cells were then made quiescent by incubating them for 24 hours in Mito Media, then washed once with 4° C. binding media. The binding activity of the PDGF-BB to its receptors was analyzed in the presence of heparin by adding two-fold dilutions of $^{125}$I-PDGF-BB in 4° C. binding media (ranging from $2\times10^5$ to $2.5\times10^4$ cpm/ml) containing 10 µg/ml heparin (Elkins-Sinn, Inc.) to the appropriate wells in triplicate in 1 ml aliquots. On a separate plate, the same dilution series of $^{125}$I-PDGF-BB was added without heparin. A set of triplicate wells on each plate also contained $2.0\times10$ cpm/well of $^{125}$I-PDGF-BB in addition to 1 µg/ml unlabeled PDGF-BB to determine the level of nonspecific binding by $^{125}$I-PDGF-BB. The plates were kept on ice while samples were being added, and then incubated for 1.5 hour at 4° C. on a rotary shaker. After washing 3× with PBS, the cells were incubated with an extraction buffer, and the extracts were harvested to 12×75 mm tubes and counted in a gamma counter.

The results, presented in Table 17, demonstrate that the presence of heparin had no significant effect on $^{125}$I-PDGF-BB binding. Thus, the combinatorial effectiveness of coordinately administering heparin with the anti-PDGFr antibodies, shown in the above examples, does not appear to be attributable to any inhibition by heparin of the binding of PDGF-BB to cell-surface PDGF receptors.

TABLE 17

| | | |
|---|---|---|
| Saturation Binding Analysis of PDGF-BB on Baboon Vascular Smooth Muscle Cells in the Presence and Absence of Heparin | | |
| $^{125}$I PDGF-BB | Mean Specific cpm +/− Std. Dev. | |
| (applied cpm) | (+) Heparin | (−) Heparin |
| 200,000 | 1,674.0 ± 15.7 | 1,800.0 ± 112.0 |
| 100,000 | 1,428.5 ± 61.0 | 1,572.0 ± 80.6 |
| 50,000 | 1,327.0 ± 91.3 | 1,438.5 ± 41.2 |
| 25,000 | 1,005.4 ± 63.7 | 1,107.8 ± 58.2 |

Example 23

Inhibition of PDGF-BD Binding to Smooth Muscle Cells By MAb 163.31 in the Presence and Absence of Heparin An experiment was carried out to determine the ability of MAb 163.31 to inhibit $^{125}$I-PDGF-BB binding to the PDGF beta-receptor on baboon vascular smooth muscle cells in the presence and absence of heparin.

Baboon smooth muscle cells (BO54) were plated at a density of 20,000 cells/well in 24-well culture plates and grown for approximately 48 hours at 37° C. in DMEM containing 10% fetal bovine serum. The cells were incubated for 24 hours in Mito Media to become quiescent, then washed once with 4° C. binding media. MAb 163.31 was diluted in binding media to the concentrations shown in Table 18, then mixed with $^{125}$I-PDGF-BB and 10 µg/ml heparin (Elkins-Sinn, Inc.), and 1 ml aliquots of the mixture were added in triplicate to wells of BO54 cells. On a separate plate, the same dilution series of 163.31 was added to $^{125}$I-PDGF-BB without heparin. A set of triplicate wells on each plate contained $^{125}$I-PDGF-BB plus 1 µg/ml unlabeled PDGF-BB to determine the level of nonspecific binding by $^{125}$I-PDGF-BB. The plates were kept on ice while samples were being added, then incubated for 1.5 hour at 4° C. on a rotary shaker. After washing 3× with PBS, the cells were incubated with an extraction buffer, and the extracts were transferred to 12×75 mm tubes and counted in a gamma counter.

The results, presented in Table 18, demonstrate that the presence of heparin had no significant effect on dose-dependent inhibitory activity of MAb 163.31 on $^{125}$I-PDGF-BB binding to BVSMCs. Thus, the combinatorial effectiveness of coordinately administering heparin with the anti-PDGFr antibodies, shown in the above examples, does not appear to be attributable to any direct modulation by heparin of the PDGF-BB binding inhibitory activity of the anti-PDGFr-beta antibody.

TABLE 18

| | | |
|---|---|---|
| Inhibition of $^{125}$I-PDGF-BB binding to Smooth Muscle Cells By MAb 163.31 in the Presence and Absence of Heparin | | |
| | Mean Specific cpm ± S.D. (percent of control) | |
| MAb 163.31 | (+) Heparin | (−) Heparin |
| 24 µg/ml | 888.0 ± 162.6 (39.5%) | 715.0 ± 70.0 (36.6%) |
| 8 µg/ml | 911.0 ± 291.3 (40.5%) | 944.0 ± 89.1 (48.3%) |
| 2.7 µg/ml | 1,176.0 ± 107.5 (52.3%) | 1,021.0 ± 27.0 (52.2%) |
| 0.9 µg/ml | 1,221.0 ± 192.9 (54.3%) | 1,136.0 ± 29.8 (58.1%) |
| 0.3 µg/ml | 1,549.0 ± 173.5 (68.9%) | 1,354.0 ± 46.4 (69.3*) |
| 0.1 µg/ml | 1,682.0 ± 104.7 (74.8%) | 1,687.0 ± 6.0 (86.3%) |
| 0.033 µg/ml | 2,174.0 ± 236.1 (96.7%) | 1,726.0 ± 92.4 (88.3%) |
| 0.0 µg/ml | 2,248.0 ± 110.3 (100.0%) | 1,955.0 ± 24.0 (100.0%) |

Example 24

Continuous Intravenous Infusion of MAbs 169.31 and 163.31 into Baboons and Analysis of the Baboon Anti-Murine IgG Response This study was designed to monitor circulating levels of the murine anti-PDGFr antibodies following continuous infusion by either intravenous or intraperitoneal routes. A pool of anti-PDGFr MAbs 163.31 and 169.31 was made with the two antibodies at approximate concentrations of 36 and 22 mg/ml, respectively. The antibodies were formulated in a physiologically acceptable carrier of 1.5% glycine, 0.2M NaCl, and 0.01% Tween-20. The antibody pool was loaded into Alzet 14 day osmotic pumps, which contain 2.1 ml of sample and deliver at a rate of approximately 5 µl/hour. Two pumps were placed into each of three experimental animals. Two of the animals had the pumps placed intraperitoneally (IP) into the peritoneal cavity, and one animal had the pumps placed into the subcutaneous space and the antibody delivered intravenously (IV) by the use of a silastic catheter placed into the venous system.

Plasma samples were collected from the experimental animals at 1, 7, 14, 21, and 28 days following pump placement. The plasma samples were analyzed for circulating levels of the anti-PDGFr antibodies by ELISA. In addition, the plasma samples were analyzed for the presence of baboon antibodies directed towards the murine antibodies.

To analyze for the presence of the murine antibodies, 96-well microtiter plates were coated with either goat anti-mouse IgG1 (Sigma Chemical Co.) or goat anti-mouse IgG2a (Boehringer-Mannheim, Indianapolis, Ind.) at 1 µg/ml in ELISA A buffer. The plates were incubated overnight at 4° C., then washed 2× with ELISA C buffer. The plates were blocked by the addition of ELISA B buffer for 2 hours at 37° C., then washed 2× with ELISA C buffer. The baboon plasma samples were diluted with ELISA B buffer, then added to the appropriate test wells. Dilutions of purified monoclonal antibodies 163.31 and 169.31, diluted in control baboon plasma were added to a set of test wells in order to generate a standard curve for use in quantifying antibody levels in the baboon plasma samples. The test antibody samples were incubated for 2 hours at 37° C., then the wells were washed 3× with ELISA C buffer. Goat anti-mouse IgG conjugated with horseradish perixidase (Tago, Burlingame, Calif.) was then added to the wells, and the plates were incubated at 37° C. for an additional 2 hours. The wells were washed with ELISA C buffer, then incubated with Reaction Buffer for approximately 1 minute. The reaction was stopped by the addition of 1N $H_2SO_4$, and the plates were read in an ELISA microtiter plate reader at 492 nm. Using the values obtained from the purified antibody samples, a standard curve was generated for each antibody, and the concentrations of the antibodies in the baboon plasma samples were determined from these curves.

The results, presented in Table 19, demonstrate that there was a peak in the circulating antibody levels at 1 day following pump placement in the i.v. infused animal, while the peak antibody levels were found at day 7 in the intraperitoneal infused animals. At days 14, 21 and 28 the circulating antibody levels were less than 1% of the peak levels measured at the earlier time points.

Example 25

Determination of Circulating Half-Life of Chimeric Anti-PDGFr-Beta Antibody in Cynomologus Monkeys Metabolism of the chimeric anti-PDGFr-beta antibody was determined in Cynomolgus monkeys. This was achieved by use of $^{125}$I-labeled antibody. Purified antibody was labeled with $^{125}$Iodine by the chloramine T method to a specific activity of approximately 10 µCi/µg of antibody. Three male Cynomolgus monkeys were used in this study, ranging in body weight from 6.0 to 6.6 kg. On the morning of the experiment the radiolabeled antibody was drawn into a 3 ml syringe and placed in an infusion pump. The monkeys were anesthetized with ketamine, and the saphenous veins were cannulated with a 24 gauge intravenous catheter (SURFLO, Terumo Medical Corp., Elkton, Md.) attached to polyethylene tubing. The syringe containing the antibody was attached to the tubing, and the infusion was begun at a rate of 0.5 ml/minute, followed by a 0.5 ml flush with saline. Each animal received a dose of 3.18 mg of antibody/kg body weight.

Immediately following the infusion, blood sampling was begun. In order to determine the half-life of the antibody, samples were drawn into EDTA-containing vacutainer tubes at 0, 0.083, 0.25, 0.5, 1, 2, 4, 8, 12, 24, 72, 120, 168, 240, 336, 504, and 672 hours. Blood was spun, plasma was decanted, and radioactivity was determined in a gamma counter (80% efficiency). Antibody concentrations in the plasma were determined by comparing the counts in the blood to the initial specific activity of the radiolabeled antibody, taking into account the decay rate for $^{125}$I. Analysis of the antibody concentrations in the plasma samples showed the half-life of the antibody to be approximately 50 hours.

TABLE 19

Circulating Levels of Anti-PDGFr Antibody Following Continuous Infusion Into Baboons

| Day | Animal A (IP) | | Animal B (IP) | | Animal C (IV) | |
|---|---|---|---|---|---|---|
| | MAb163 | MAb 169 | MAb163 | MAb169 | MAb163 | MAb169 |
| 1 | 1000 | 1600 | 340 | 600 | 8000 | 6400 |
| 7 | 9000 | 7000 | 4000 | 3200 | 2500 | 200 |
| 14 | 14 | 64 | 5 | 6 | 8 | 40 |
| 21 | 8 | 50 | 5 | 8 | 4 | 18 |
| 28 | 7 | 40 | 1 | 2 | 3 | 14 |

Data are presented as ng/ml of circulating levels of the anti-PDGFr MAbs in baboon plasma at various times following the initiation of antibody infusion. IP: Intraperitoneal infusion, IV: Intravenous infusion.

Studies to measure potential baboon antibody generated against the infused murine antibodies were performed using ELISA. The results suggested that the low levels of circulating antibody measured at 14 days were due to an immune response generated in the baboons against the murine antibodies. These findings suggest that to provide a sustained level of circulating anti-PDGFr antibody in a primate system, it is useful to select antibodies so as to minimize their immunogenic potential. This can be done by a variety of conventional means, including by making Fab or F(ab')2 fragments, or by constructing mouse/human chimeric antibodies or other antibody fragments or constructs with decreased immunogenicity.

Example 26

Development of a Sequential Arterial Injury Model in Baboons for Testing Antihyperplastic Agents and Treatments Following Vascular Injury A model of sequential arterial injury was developed in the baboon to allow testing of the anti-PDGFr antibodies for their ability to inhibit experimentally induced intimal hyperplasia in primates. This model was designed to allow each animal to act as its own control by utilizing bilateral arterial injuries introduced at 28 day intervals.

Baboons weighing approximately 10 kg each were used in this study. The initial surgical procedure closely resembled the vascular reconstructive procedure of balloon angioplasty used in clinical applications for treatment of human atherosclerosis. For each animal, an initial balloon denudation pull-back injury was made to the saphenous artery. On day 28 the animals underwent a second surgical procedure whereby the initially injured artery was excised, and the excised artery was perfusion-fixed ex vivo under 100 mm Hg pressure for 1 hour with a 10% formalin solution. Following excision of the first artery, the contralateral saphenous artery received a ballon denudation injury. Following the second 28-day period the second injured artery was excised and perfusion fixed ex vivo in a similar manner as the first artery.

Both of the excised arteries were separated into multiple sections and embedded in paraffin. Sections were cut from multiple tissue blocks, stained with hematoxylin and eosin, then analyzed by morphometric analysis for intimal lesion formation using a computerized image analysis system (Ferns et al., Science 253:1129, 1991).

The results of the study, presented in Table 20, demonstrate that the intimal/medial ratios (I/M) for the contralateral arteries were very similar, even though the initial arterial injuries were made 28 days apart. This suggests that the presence of an initial arterial injury, and the subsequent removal of the injured arterial segment, does not effect the response of the second injured artery. These results also demonstrate that the extent of arterial injury, as measured by the intimal/medial ratio, is more similar within an animal than between animals. These findings demonstrate that it is possible to utilize a sequential injury model, whereby each animal acts as its own control, for evaluating the efficacy of therapeutic compounds to inhibit intimal lesion formation in the baboon.

TABLE 20

Analysis of Intimal Lesion Development Following Sequential Balloon Denudation Arterial Injuries in the Baboon

| Animal | Side | Intimal Area (mm$^2$) | Medial Area (mm$^2$) | I/M Ratio |
| --- | --- | --- | --- | --- |
| Z6 | R | 0.1256 | 1.085 | 0.1151 |
| Z6 | L | 0.0543 | 0.547 | 0.0995 |
| Z8 | R | 0.1877 | 1.269 | 0.1493 |
| Z8 | L | 0.1125 | 0.826 | 0.1344 |

Example 27

Evaluation of Anti-PDGF Receptor Antibody/Heparin Therapy to Inhibit Intimal Hyperplasia in Primates Baboons weighing approximately 10 kg each are used to study the efficacy of anti-PDGFr MAbs and heparin. An initial balloon denudation pull-back injury is made to one saphenous artery of the animal. Additional arterial beds, such as the radial, brachial, carotid or femoral arterial beds, may also be used. At the time of injury a femoral vein catheter and subcutaneous (SQ) osmotic pump are inserted (twenty-eight day pumps, two pumps per animal). The pumps deliver a combined rate of 5 µl/hour. During the first 28-day control period the pumps are loaded with placebo saline solution.

During the 28-day period following the balloon injury, the animals receive i.v. injections of placebo buffer. Typical injection times are 0, 3, 7, 14 and 21 days following the initial injury.

On day 27 one-half of the animals receives three intramuscular (IM) injections, 8 hours apart, of bromodeoxyuridine (Brdu) to allow for labeling of replicating cells in the artery wall.

On day 28 a second surgical procedure is performed whereby the previously injured artery is excised and perfusion-fixed under 100 mm Hg pressure for 1 hour with a 10% formalin solution. Following excision of the first artery, the contralateral saphenous artery receives a ballon denudation injury. Femoral vein catheters and SQ osmotic pumps are then inserted. The pumps are loaded with unfractionated heparin (Elkins-Sinn, Inc.) to be delivered at the rate of approximately 0.1 mg/kg/hour. Circulating levels of heparin are monitored using a commercially available kit (American Diagnostica).

The animals receive an i.v. injection of mouse/human chimeric anti-PDGF receptor antibody one hour prior to the second balloon injury, followed by i.v. injections at days 3, 7, 14 and 21 post-angioplasty. A dose of 10 mg/kg of the anti-PDGF receptor antibody is used to give an initial circulating level of 350 µg/ml and a level of approximately 20 µg/ml at 7 days (based on a $T_{1/2}$ for the chimeric antibody of approximately 50 hours in cynamolgus monkeys).

Blood draws are done on a weekly basis at the time of antibody injection to determine the circulating levels of anti-PDGF receptor antibody and circulating levels of heparin. Circulating antibody levels are determined using an ELISA. Heparin levels are determined as described above. In addition, animals are monitored for any baboon antibody response directed towards the chimeric antibody. If a positive serum titer is detected, the antisera are measured for neutralizing activity towards the chimeric antibody.

Following the second 28-day period, the second injured artery is excised and perfusion-fixed ex vivo in a similar manner as the first artery. In addition, those animals not treated with Brdu at the time of the excision of the first artery are now treated with bromodeoxyuridine to label replicating cells in the artery wall as was done at the time of harvesting the control arteries.

Both the control arteries and the arteries harvested following antibody treatment are separated into multiple sections and embedded in paraffin. Sections are cut from multiple tissue blocks and stained with hematoxylin and eosin, then analyzed by morphometric analysis for intimal lesion formation using a computerized image analysis system (Ferns et al., Science 253: 1129, 1991) Separate sections are stained with an anti-Brdu antibody (Boehringer-Mannheim, Inc.) to determine the level of replicating cells in each tissue section.

Preliminary studies, disclosed above, using the sequential injury model demonstrated that there was low variability between the arteries injured 28 days apart. Analysis of preliminary studies suggested that an n=15 would be required to observe a 50% decrease in lesion development with a 95% confidence limit.

Data obtained from the multiple sections from each artery are pooled to obtain a single lesion number for each artery. The control and test artery for each animal are compared in a paired format to determine the significance of antibody treatment to decrease intimal lesion development. Similar analysis is used to measure the level of intimal and medial cell replication rates, determined by staining for Brdu.

A similar protocol is used for evaluation of a pooled anti-PDGF alpha receptor (MAb 169.3.1) and anti-PDGF beta receptor (MAb 163.3.1) antibody preparation, as well as for the two chimeric antibodies individually.

The protocol described above can be used to evaluate the anti-PDGF receptor antibodies individually, in combination, or in the the presence or absence of various doses of heparin. In addition to using morphometric analysis to look for changes in intimal hyperplasia, additional types of analysis that can be used to monitor lesion formation include angiography, intravascular ultrasound, and nuclear magnetic resonance scanning. In addition, tissue samples can be obtained from the site of injury at multiple time points following the induction of the injury by reduction athectomy.

Although the foregoing invention has been described in some detail by way of illustration and example for purposes of clarity of understanding, it will be evident that certain changes and modifications may be practiced within the scope of the appended claims.

We claim:

1. A method of inhibiting intimal hyperplasia in the vasculature of a mammal, comprising:

administering to said mammal an antihyperplastically effective amount of an anti-platelet derived growth factor (PDGF) beta receptor antibody.

2. A method according to claim 1, wherein said antibody inhibits one or more intimal hyperplastic processes selected from the group consisting of vascular smooth muscle cell proliferation, vascular smooth muscle cell migration, and neointimal deposition of extracellular matrix.

3. A method according to claim 1, wherein said antibody inhibits binding of PDGF to PDGF beta receptors.

4. A method according to claim 1, wherein said mammal is a primate.

5. A method according to claim 1, wherein said antibody is a monoclonal antibody.

6. A method according to claim 1, wherein said antibody is administered concurrently with, or within an antihyperplastically effective time period before, an occurrence of acute vascular injury in said mammal.

7. A method according to claim 6, wherein said injury is due to vascular reconstruction.

8. A method according to claim 7, wherein said vascular reconstruction comprises angioplasty, endarterectomy, reduction atherectomy, or anastomosis of a vascular graft.

9. A method according to claim 1, wherein said antibody is administered within an antihyperplastically effective time period following an occurrence of acute vascular injury in said mammal.

10. A method according to claim 9, wherein said injury is due to vascular reconstruction.

11. A method according to claim 10, wherein said vascular reconstruction comprises angioplasty, endarterectomy, reduction atherectomy or anastomosis of a vascular graft.

12. A method according to claim 1, wherein said antibody is administered concurrently with, or within an antihyperplastically effective time period before, emplacement of a vascular graft or transplanted organ.

13. A method according to claim 1, wherein said antibody is administered within an antihyperplastically effective time period following emplacement of a vascular graft or transplanted organ.

14. A method according to claim 1, wherein a panel of anti-PDGF beta receptor antibodies is administered to said mammal.

15. A method according to claim 1, wherein said antibody is a humanized monoclonal antibody.

16. A method according to claim 1, wherein said antibody is a single chain antibody.

17. A method according to claim 1, wherein said antibody is a chimeric antibody.

18. A method according to claim 17, wherein said antibody is a human-mouse chimeric antibody.

19. A method according to claim 18, wherein said chimeric antibody comprises mouse variable domains operably linked to human constant domains.

* * * * *